(12) United States Patent
Heidler

(10) Patent No.: US 6,714,009 B2
(45) Date of Patent: Mar. 30, 2004

(54) METHOD FOR THE INVERSION OF CPMG MEASUREMENTS ENHANCED BY OFTEN REPEATED SHORT WAIT TIME MEASUREMENTS

(75) Inventor: Ralf Heidler, Richmond, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/147,749

(22) Filed: May 16, 2002

(65) Prior Publication Data

US 2003/0214286 A1 Nov. 20, 2003

(51) Int. Cl.[7] ................................ G01V 3/00
(52) U.S. Cl. ........................................ 324/303
(58) Field of Search ......................... 324/303

(56) References Cited

U.S. PATENT DOCUMENTS

| | | | | |
|---|---|---|---|---|
| 5,486,762 | A | * | 1/1996 | Freedman et al. ........... 324/303 |
| 5,629,623 | A | | 5/1997 | Sezginer et al. |
| 5,914,598 | A | | 6/1999 | Sezginer et al. |
| 6,121,774 | A | * | 9/2000 | Sun et al. .................... 324/303 |
| 6,140,818 | A | * | 10/2000 | Hurlimann ................... 324/303 |
| 6,229,308 | B1 | * | 5/2001 | Freedman .................... 324/303 |
| 6,232,778 | B1 | | 5/2001 | Speier et al. |
| 6,237,404 | B1 | | 5/2001 | Crary et al. |
| 6,246,236 | B1 | | 6/2001 | Poitzsch et al. |
| 6,255,817 | B1 | | 7/2001 | Poitzsch et al. |
| 6,291,995 | B1 | | 9/2001 | Speier et al. |
| 6,297,632 | B1 | * | 10/2001 | Speier ......................... 324/303 |
| 6,326,784 | B1 | * | 12/2001 | Ganesan et al. ............. 324/303 |
| 6,366,089 | B1 | | 4/2002 | Poitzsch et al. |
| 6,369,567 | B1 | * | 4/2002 | Song et al. .................. 324/303 |
| 6,373,248 | B1 | | 4/2002 | Poitzsch et al. |
| 6,392,409 | B1 | * | 5/2002 | Chen ........................... 324/303 |
| 6,392,410 | B2 | | 5/2002 | Luong et al. |
| 6,400,149 | B1 | | 6/2002 | Luong et al. |
| 6,492,809 | B1 | | 12/2002 | Speier et al. |
| 6,518,757 | B1 | | 2/2003 | Speier |
| 6,518,758 | B1 | | 2/2003 | Speier et al. |
| 6,525,534 | B2 | * | 2/2003 | Akkurt et al. ............... 324/303 |
| 6,528,995 | B1 | | 3/2003 | Speier et al. |
| 6,531,869 | B1 | | 3/2003 | Speier et al. |
| 6,538,438 | B1 | | 3/2003 | Speier et al. |
| 6,541,969 | B2 | * | 4/2003 | Sigal et al. .................. 324/303 |
| 6,566,874 | B1 | | 5/2003 | Speier et al. |
| 6,570,381 | B1 | | 5/2003 | Speier et al. |

* cited by examiner

Primary Examiner—Diego Gutierrez
Assistant Examiner—Dixomara Vargas
(74) Attorney, Agent, or Firm—Kevin P. McEnaney; John J. Ryberg; Brigitte L. Jeffery

(57) ABSTRACT

A method for determining an earth formation property from nuclear magnetic resonance measurements includes applying suppression functions to spin echoes in at least one burst measurement set to produce a modified burst data set, the suppression functions to suppress contribution of spin echoes having non-negligible polarization correction; inverting the modified burst data set and at least one standard spin echo measurement set to produce a nuclear magnetic resonance parameter distribution, the at least one standard spin echo measurement set and the at least one burst measurement set being acquired on an earth formation sample; and computing the earth formation property from the nuclear magnetic resonance parameter distribution. The nuclear magnetic resonance parameter includes at least one selected from longitudinal relaxation time, transverse relaxation time, a ratio of longitudinal relaxation time to transverse relaxation time, and diffusion constant.

38 Claims, 16 Drawing Sheets

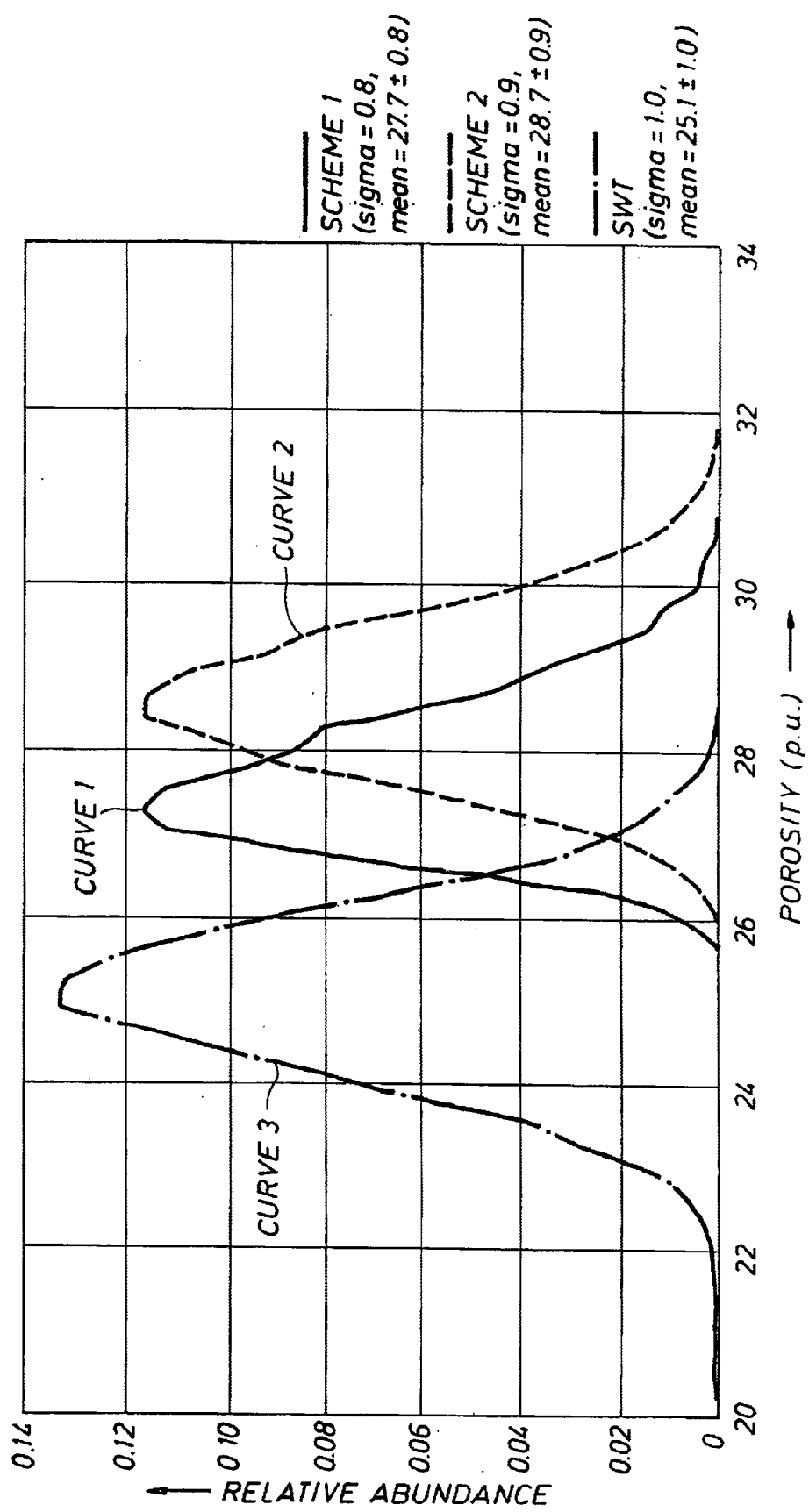

METHOD FOR THE INVERSION OF CPMG MEASUREMENTS ENHANCED BY OFTEN REPEATED SHORT WAIT TIME MEASUREMENTS

BACKGROUND OF INVENTION

1. Field of the Invention

The invention relates generally to the field of well logging. More particularly, the invention relates to techniques for well logging using nuclear magnetic resonance tools and methods for inversion processing of nuclear magnetic resonance data.

2. Background Art

Oil well logging tools include nuclear magnetic resonance (NMR) instruments. NMR instruments can be used to determine properties of earth formations, such as the fractional volume of pore space, the fractional volume of mobile fluid filling the pore space, and the total porosity of earth formations. General background of NMR well logging is described in U.S. Pat. No. 6,140,817, assigned to the assignee hereof.

Signals measured by NMR logging tools typically arise from selected nuclei present in the probed volume. Because hydrogen nuclei are the most abundant and easily detectable, most NMR logging tools are tuned to detect hydrogen resonance signals (from either water or hydrocarbons). Hydrogen nuclei have different dynamic properties (e.g., diffusion rate and rotation rate) that are dependent on their environments (e.g., bound to pore surfaces versus free in fluids). The different dynamic properties of these nuclei manifest themselves in different nuclear spin relaxation times (i.e., spin-lattice relaxation time ($T_1$) and spin—spin relaxation time ($T_2$)). For example, hydrogen nuclei in viscous oils have relatively short relaxation times whereas hydrogen nuclei in light oils have relatively long relaxation times. Furthermore, the hydrogen nuclei in the free water (e.g., water in large vugs) typically have longer relaxation times than those in the bound water (e.g., clay-bound water). Consequently, these differing NMR relaxation times can provide information on properties of the earth formations.

Most NMR logging tools measure the spin—spin relaxation times ($T_2$) to derive the properties of the earth formations. $T_2$ relaxation is often measured from a train of spin-echoes that are generated with a series of pulses such as the Carr-Purcell-Meiboom-Gill (CPMG) pulse sequence or some variants of this. The CPMG pulse sequence is well known in the art. See Meiboom, S., Gill, D., 1958, "Modified Spin Echo Method for Measuring Nuclear Relaxation Times," Review of Scientific Instruments, 29, 688–91.

Once the NMR data are acquired, they are processed with any of a number of inversion methods known in the art to provide the desired information, for example, $T_2$ distributions, from which the formation properties may be derived. The inversion of NMR data (e.g., the CPMG data) to provide accurate $T_2$ distributions is a challenging problem because NMR measurements include information from fast and slow relaxing nuclei. Under well logging conditions, the long relaxing nuclei may not have sufficient time to fully relax (i.e., to be fully polarized by the static magnetic field). This necessitates polarization corrections before the NMR data are analyzed. On the other hand, the fast relaxing nuclei (e.g., those from clay-bound water) would have fully relaxed within a short wait time. Signals from these fast relaxing nuclei last only a few echoes and become undetectable afterwards. As a result, most of the collected spin echoes contain nothing but noise with respect to the fast relaxing nuclei, and accurate derivation of $T_2$ distribution for the fast relaxing nuclei becomes difficult using conventional well logging and processing techniques.

Because fast $T_2$ relaxation nuclei are generally associated with short $T_1$ relaxation, the fast $T_2$ relaxing nuclei can be better detected with rapidly repeated short wait time measurements (bursts). The high repetition rate of these burst measurements allows a better statistical averaging of signals from the fast $T_2$ components. For example, U.S. Pat. No. 6,005,389 issued to Prammer (the Prammer patent) discloses a method of collecting NMR data with fast repeated pulse sequences that produce an improved signal to noise ratio (SNR) for the fast relaxing nuclei by stacking (averaging) of the measured data.

The $T_2$ inversion of these bursts together with a standard CPMG measurement, however, poses some difficulty. If one were to combine these measurements in a common inversion process, one would need a good knowledge of the polarization correction for the burst measurements so that the residual contribution from partially polarized slow relaxing nuclei can be removed. "A common inversion" as used herein means a single inversion process using both measurements. Alternatively, a simplified assumption about the relation between polarization and $T_2$ (or between $T_1$ and $T_2$) could be made so that a polarization correction term can be determined from two different wait time measurement sets. In an alternative approach, the burst measurements and the standard CPMG measurements may be separately inverted to produce independent $T_2$ distributions, which are later combined to produce a common $T_2$ distribution. See e.g., the Prammer patent. However, combining (or splicing) the two distributions into a common $T_2$ distribution may result in less accurate inversion output.

Therefore, it is desirable to have methods that use common inversion on dual wait time measurements, but avoid problems associated with imperfect polarization corrections in the burst measurements.

SUMMARY OF INVENTION

One aspect of the invention relates to methods for inverting NMR measurements from well logging. According to embodiments of the invention, a method for determining an earth formation property from nuclear magnetic resonance measurements may include applying suppression functions to spin echoes in at least one burst measurement set to produce a modified burst data set, the suppression functions to suppress contribution of spin echoes having non-negligible polarization correction; inverting the modified burst data set and at least one standard spin echo measurement set to produce a nuclear magnetic resonance parameter distribution, the at least one standard spin echo measurement set and the at least one burst measurement set being acquired on an earth formation sample; and computing the earth formation property from the nuclear magnetic resonance parameter distribution. The nuclear magnetic resonance parameter includes at least one selected from longitudinal relaxation time, transverse relaxation time, a ratio of longitudinal relaxation time to transverse relaxation time, and diffusion constant. The suppression functions may comprise linear combination functions. The linear combination functions may comprise a null space of a matrix describing exponential decays of nuclear magnetizations according to acquisition parameters. The null space may be determined by singular value decomposition.

Another aspect of the invention relates to methods for determining a property of earth formations surrounding a wellbore using NMR instruments. In some embodiments of the invention, a method for determining a property of earth formations surrounding a wellbore may include inducing a static magnetic field in an area of investigation in the earth formations; acquiring at least one standard spin echo measurement set and at least one burst measurement set by applying spin echo pulse sequences comprising radio frequency magnetic field pulses in the area of investigation and receiving spin echo signal magnitudes; applying suppression functions to spin echoes in at least one burst measurement set to produce a modified burst data set, the suppression functions to suppress contribution of spin echoes having non-negligible polarization correction; and computing the property of the earth formations from the at least one standard spin echo measurement set and the modified burst data set.

Other aspects and advantages of the invention will be apparent from the following description and the appended claims.

BRIEF DESCRIPTION OF DRAWINGS

FIG. 6 is a chart of sensitivities for each column vector of matrix X computed using the singular values from the fourth one on.

FIG. 17 is a chart illustrating the probability distributions of porosity from the two inversion schemes using the Monte Carlo simulations with the $T_2$ distribution shown in FIG. 15.

DETAILED DESCRIPTION

Figures 1, 2:
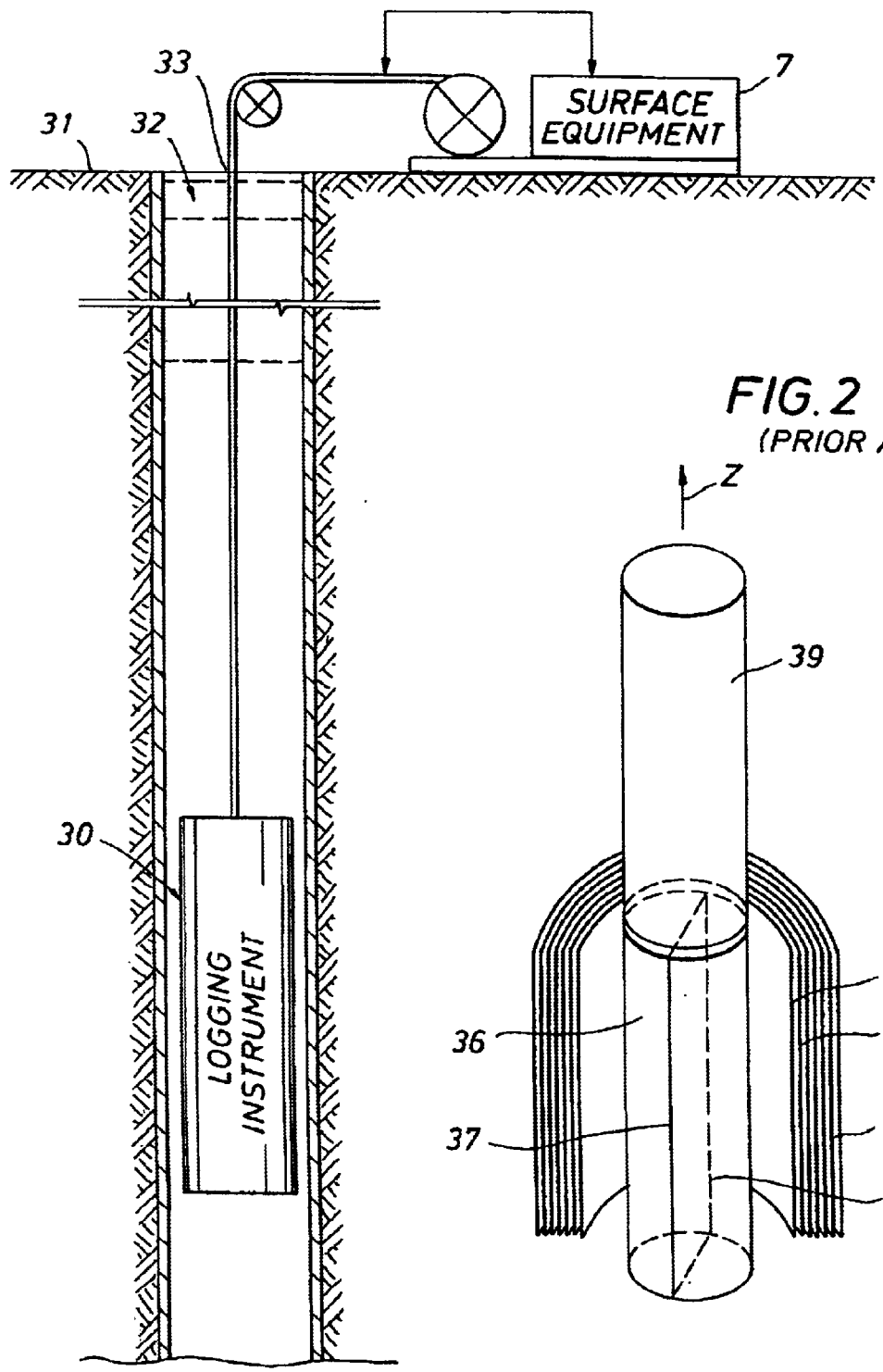
FIG. 1 is a diagram of a typical setup for well logging.
FIG. 2 shows a diagram of an NMR logging tool.

FIG. 1 shows a schematic of a nuclear magnetic resonance (NMR) logging tool 30 for investigating earth formations 31 traversed by a borehole 32. The NMR logging tool 30 is suspended in the borehole 32 on an armored cable 33, the length of which substantially determines the relative depth of the logging tool 30. The cable length is controlled by suitable means at the surface such as a drum and winch mechanism 7A. Surface equipment 7 may include a processor subsystem to communicate with downhole equipment including NMR logging tool 30.

The NMR logging tool 30 can be any suitable nuclear magnetic resonance logging device. It may be one adapted for in wireline logging applications as shown in FIG. 1, or one that can be used in logging while drilling (LWD) applications. The NMR logging tool 30 typically includes a means for producing a static magnetic field in the formations, at least one radio frequency (RF) antenna, and means for producing pulses of RF power to induce RF magnetic fields in the formations and for receiving the spin echoes from the formations. The means for producing a static magnetic field may comprise a permanent magnet or magnet array, and the RF antenna may comprise one or more RF antennas, which may be solenoid antennas, loop antennas, or saddle antennas.

A schematic representation of some of the components of the NMR logging tool 30 is illustrated in FIG. 2, which shows a first centralized magnet or magnet array 36 and an RF antenna 37, which may be a suitably oriented coil or coils. FIG. 2 also illustrates a general representation of closely-spaced cylindrical thin shells, 38-1, 38-2 ... 38-N, that can be frequency selected in a multi-frequency logging operation. These thin shells are resonance regions where magnet 36 has a radial gradient in the field amplitude. One such device is disclosed in U.S. Pat. No. 4,710,713 issued to Taicher et al. In FIG. 2, another magnet or magnet array 39 is shown. Magnet array 39 may be used to pre-polarize the earth formation ahead of the investigation region as the logging device 30 is raised in the borehole in the direction of arrow Z. Examples of NMR logging tools having pre-polarization magnet arrays are disclosed in U.S. Pat. Nos. 5,055,788 and 3,597,681.

Figure 3:
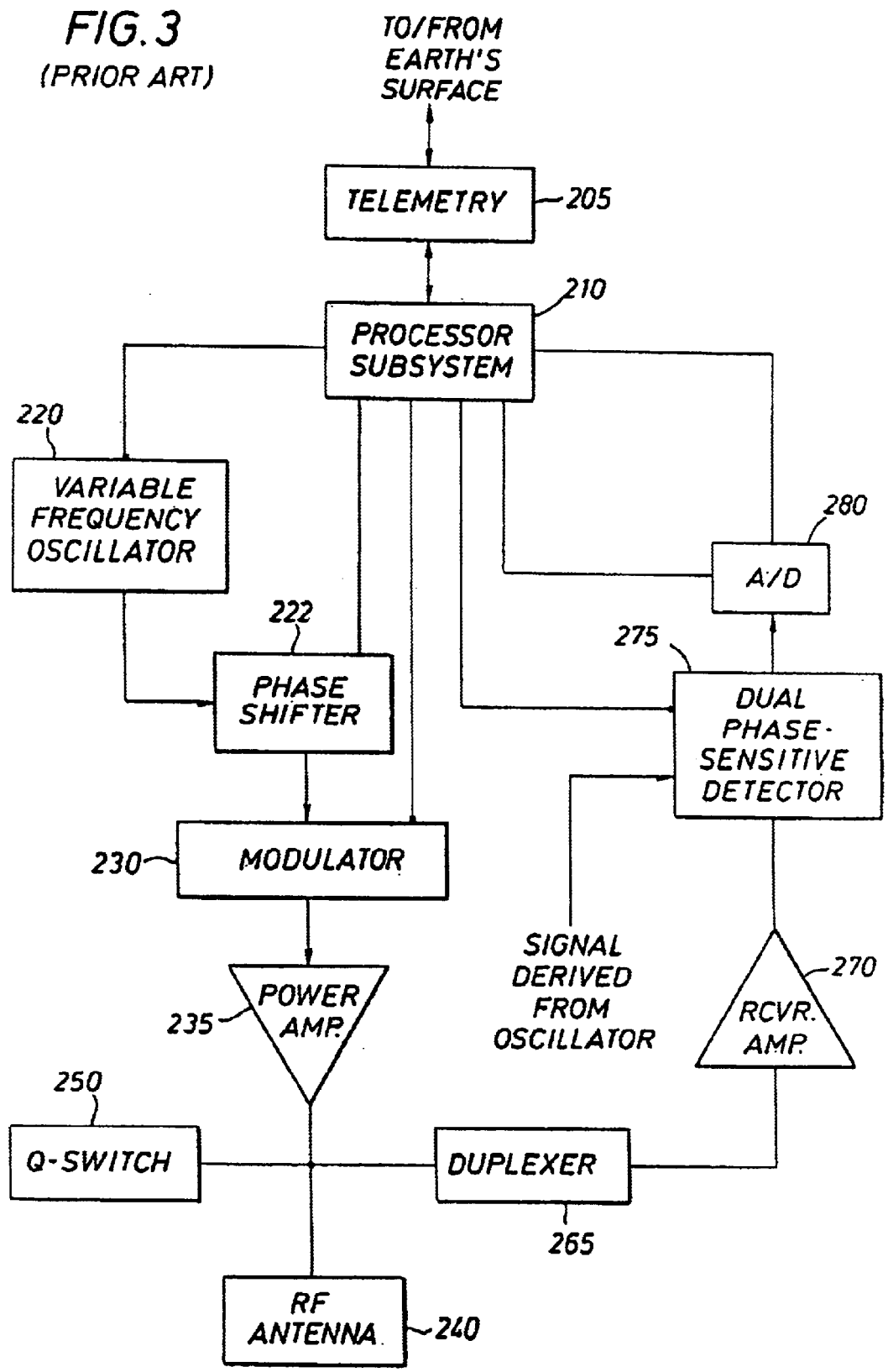
FIG. 3 is a block diagram of circuitry for producing RF pulses and receiving the spin echoes.

FIG. 3 illustrates a schematic of circuitry of an NMR tool for producing the RF pulses and for detecting spin echoes. One skilled in the art would appreciate that any other suitable circuitry could be used without departing from the scope of the invention. In FIG. 3, a downhole processor 210 has associated memory, timing, interfaces, and peripherals (not separately shown), as known in the art. The processor subsystem 210 is coupled with telemetry circuitry 205, for communication with a processor (not shown) at the earth's surface. The pulse forming circuitry includes a variable frequency oscillator 220 which, under control of processor 210, produces radio frequency (RF) signals at the desired frequencies. The output of oscillator 220 is coupled to a phase shifter 222, which permits control of pulse phases, and then to a modulator 230, both of which are under the control of processor subsystem 210. The phase shifter 222 and modulator 230 can be controlled, in a manner known in the art, to produce the desired pulse phases of RF field. The output of modulator 230 is coupled, via a power amplifier 235, to the RF antenna 240. A Q-switch 250 can be provided to damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 acts as a low impedance connection from antenna 240 to the receiver amplifier 270. The output of receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal. Although the logging device or tool 30 is shown as a single body in FIG. 1, it may alternatively comprise separate components, and the tool may be combinable with other logging tools. Also, while a wireline tool is illustrated in FIG. 1, alternative forms of physical support and communicating link can be used, for example in a measurement while drilling system.

Several NMR parameters may be measured that can be used to derive formation properties. Most NMR logging operations measure the spin-lattice (longitudinal) relaxation times ($T_1$) and/or spin—spin (transverse) relaxation times ($T_2$) of hydrogen nuclei. In addition, some NMR logging tools may provide a ratio of $T_1/T_2$ directly, and other NMR tools may provide diffusion constants (D). All these measurements are typically acquired as a train of spin echoes using a pulse sequence such as the Carr-Purcell-Meiboom-Gill (CPMG) pulse sequence or some variant of this.

Figure 4A:
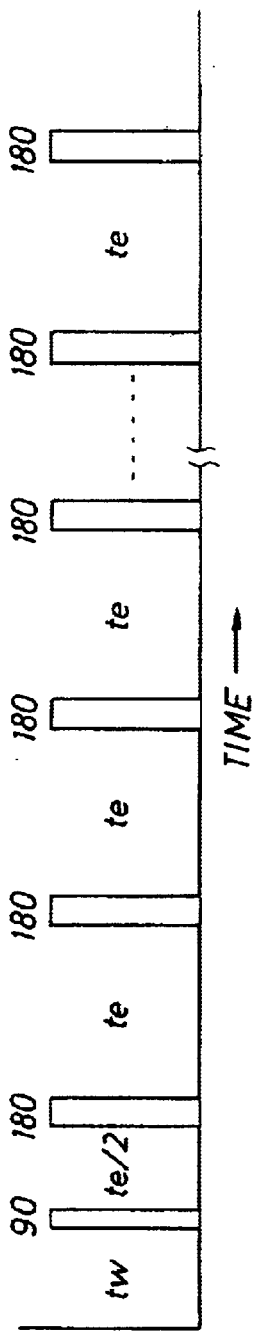
FIGS. 4A–4C illustrate a typical Carr-Purcell-Meiboom-Gill (CPMG) pulse sequence, the corresponding spin echoes for a long $T_2$ signal, and the corresponding spin echoes for a short $T_2$ signal, respectively.
Figure 4B:
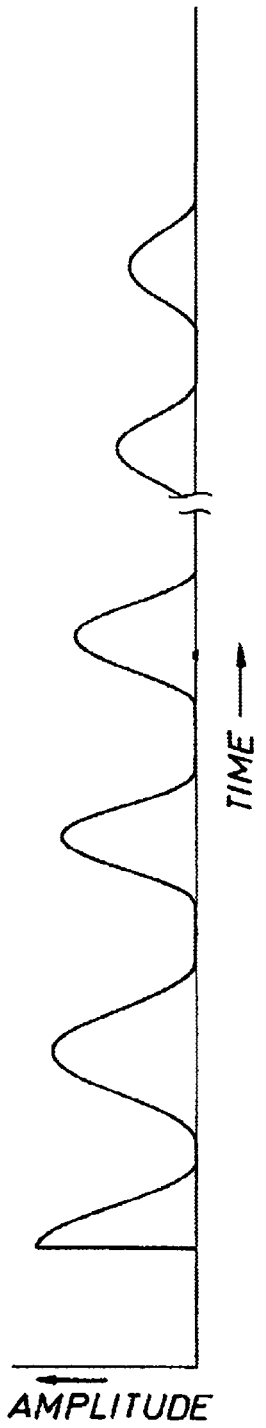
Figure 4C:
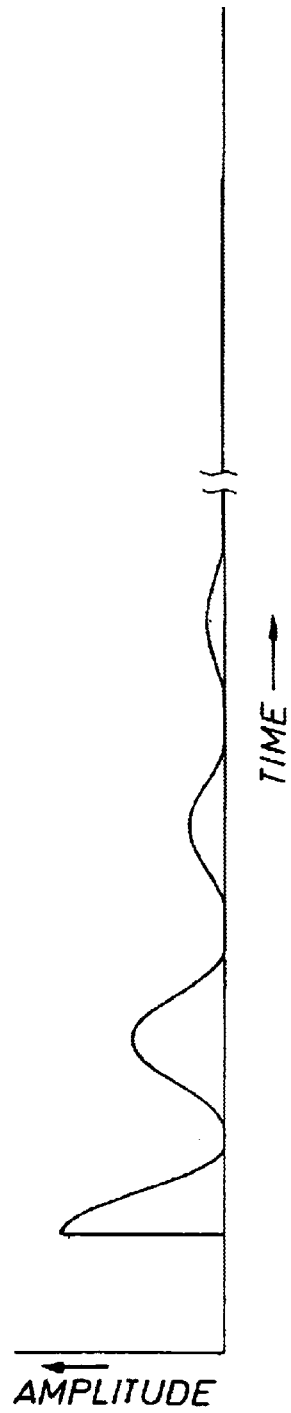

FIG. 4A depicts a CPMG pulse sequence, with the corresponding detectable signals after each pulse shown in FIG. 4B and FIG. 4C for a slow relaxing spin and a fast relaxing spin, respectively. A CPMG pulse sequence, as shown in FIG. 4A, comprises a 90-degree pulse (excitation pulse) that is applied after a wait time ($t_w$), which allows nuclear magnetizations to be polarized by the static magnetic field. After a short delay ($t_e/2$), a train of 180-degree pulses (inversion or refocusing pulses), each separated by a $t_e$ delay ("inter-echo delay"), is applied. The initial 90-degree (excitation) pulse applied along the X-axis (pulse direction is controlled by the phase shifts produced by the phase shifter 222 and modulator 230 as shown in FIG. 3) nutates the nuclear magnetizations onto the XY plane (with respect to the Z axis of the static magnetic field). During the $t_e/2$ decay that follows (first free evolution period), the magnetization in the XY plane decays rapidly primarily due to inhomogeneities of the magnetic field either due to the inherent field geometry of the tool or due to paramagnetic impurities in the sample. These magnetic field inhomogeneities cause slightly different precession frequencies (Larmor frequencies) for the different nuclei, which in turn cause phase differences between the spins and thus the rapid decay of the macroscopic magnetization in the XY plane, as shown in the "half" spin echo after the 90-degree pulses in FIGS. 4B and 4C. This is also known to the skilled artisan as Free Induction Decay (FID).

Each of the subsequent 180-degree pulses, which are applied along the Y-axis, then nutates the nuclear magnetizations by 180 degrees around the Y-axis. This rotation causes the different spins to gain an additional phase in the XY plane such that they begin to regain their phase correlation and thus form a re-appearing macroscopic magnetization, the spin echo. This process can be repeated multiple times so that after each 180-degree pulse, a spin echo is formed as shown in FIGS. 4B and 4C, which show signal amplitudes as a function of time. The amplitudes of the thus observed echoes decays with a characteristic decay time $T_2$, the spin—spin or transverse relaxation time (the heights of the echoes shown in FIGS. 4B and 4C). Because spin-lattice relaxation mechanisms also lead to an echo decay, the transverse relaxation time $T_2$ has to be smaller or at most equals the longitudinal relaxation time $T_1$. Analysis of the exponential decay of the echo train with respect to time would provide the $T_2$ values. Each 180-degree pulse also inverts any nuclear magnetizations that are in the Z-axis direction (as the result of $T_1$ relaxation during the preceding delay) onto the −Z-axis direction. These successive 180-degree pulses prevent the $T_1$ relaxation effect (return of the nuclear magnetizations to the Z-axis direction) from being cumulative and thus prevents a build-up of magnetization along the Z-axis during the echo sequence.

In well logging, a CPMG experiment typically collects hundreds to thousands of spin echoes in each pulse sequence. The signal magnitude of the i-th echo, $g_i$, in a CPMG measurement of a homogeneous sample of identical spins is determined by the number of spins in the sample, the transverse relaxation time $T_2$, the inter-echo spacing $t_e$, and the polarization of the spins due to the action of the static magnetic field $B_o$ during the wait time $t_w$. Thus, $$g_i = a \times e^{-it_e/T_2}(1 - e^{-t_w/T_1}) \tag{1}$$

The second term in equation (1).

$$(1 - e^{-t_w/T_1}),$$

describes the polarization during the wait time ($t_w$), while the pre-factor a depends on the number of spins in the sample and on environmental factors (e.g., temperature).

In a natural rock sample or earth formation, there will always be different spins (nuclear magnetizations) with different physical properties within the sample, hence different $T_1$ and $T_2$. The spin echoes measured with such a sample will be a superposition of different spin signals. In this case, $g^i$ is defined as:

$$g_i = \int\int a(T_2, T_1)e^{-it_e/T_2}(1 - e^{-t_w/T_1})dT_1 dT_2 \tag{2}$$

where the function $a(T_2, T_1)$ describes a two-dimensional (2D) spin density distribution with respect to the relaxation times $T_1$ and $T_2$. To determine the 2D spin density distribution, $a(T_2, T_1)$, it is necessary to perform many different experiments that probe the $T_1$ and $T_2$ relaxation processes independently. Because these measurements are time consuming, processes known in the art use a simplifying assumption that $T_1$ and $T_2$ are correlated, i.e., $T_1 = f(T_2)$. This assumption is justified in some situations. For example, in bulk liquids, $T_1 = T_2$. Furthermore, in general, the relation $T_2 \leq T_1$ is true. Even though this assumption may not be valid in some situations, for example, rock-bound fluids, it is necessary for all multi wait time $T_2$ inversions. When this assumption is justified, equation (2) may be simplified as:

$$g_i = \int a(T_2)e^{-it_e/T_2}(1 - e^{-t_w/f(T_2)})dT_2 \tag{3}$$

where $a(T_2)$ is the $T_2$ distribution of the spins (nuclear magnetizations).

To efficiently calculate the $T_2$ distribution, the range of interesting (or detectable) relaxation times, $T_{2min} < T_2 < T_{2max}$, is sampled on a logarithmic scale. Typically, this range, $T_{2min} < T_2 < T_{2max}$, is separated into n discrete values, i.e., $T_{2j} \forall j=0, 1, 2, \ldots n$. Thus, equation (3) can be written as:

$$\vec{g} = M\vec{a} \quad (4)$$

where $\vec{g}$ is a vector formed out of the spin echoes, vector $\vec{a}$ is the $T_2$ distribution, and matrix M is defined as:

$$M_{ij} = e^{-it_e/T_{2j}}\left(1 - e^{-t_w/f(T_{2j})}\right) \quad (5)$$

Thus, each i-th row in matrix M describes the i-th spin echo as contributions from all $T_2$ components and each j-th column in matrix M describes a mono exponential decay of a spin with amplitude 1.0 and relaxation time $T_{2j}$. The term on the right hand side of equation (4), $M\vec{a}$, is known in the art as a "forward model."

The least square solution for $\vec{a}$ without positivity constraint may be computed as:

$$\vec{a} = (M'M)^{-1}M'\vec{g} \quad (6)$$

However, the solution for a often cannot be precisely determined due to noise that is inherent in the measurements. To minimize the effects of experimental noise, a regularization term is often applied in the computation. Thus, the least square solution for $\vec{a}$ with regularization may be calculated as:

$$\vec{a} = (M'M + \lambda I)^{-1}M'\vec{g} \quad (7)$$

where $\lambda$ is a regularization parameter.

In an alternative approach, the solution $\vec{a}$ with regularization (as shown in equation (7)) can be found as the minimum of the following function:

$$F(\vec{a}) = \|M\vec{a} - \vec{g}\|^2 + \lambda\|\vec{a}\|^2 \quad (8)$$

The $T_2$ distribution is typically obtained by a constrained minimization of equation (8), in which the solution $\vec{a}$ is restricted to positive components only (this is called "positivity constraint"). Positivity constraint is based on the rationale that $T_2$ distributions derived from standard CPMG measurements should not have any negative magnitudes.

With typical inversion procedures, the echo signals of fast relaxing components (i.e., those with short $T_2$ relaxation times) are very difficult to invert because these components only appear in a few early echoes (see FIG. 4C), while a majority of the acquired echoes in a standard CPMG experiment have only noises with respect to fast relaxing components. This problem is further compounded by regularization that is used in typical inversion procedures because the regularization term, as shown in equation (7), tends to suppress fast decaying components.

One approach to alleviate these problems is to have improved signal-to-noise ratios (SNR) for the fast decaying components. Good SNR is particularly important for the resolution of short $T_2$ components. See U.S. Pat. No. 6,377,042 B1 issued to Menger et al. and references therein. To improve the SNR for the fast decaying components, these signals can be acquired using rapid repetition so as to have more signal averaging (stacking) within the same period of time. Rapid repetition is feasible because short $T_2$ components typically also have short $T_1$ relaxation times, and, therefore, do not need a long wait time to be fully polarized. The rapidly repeated measurements can then be combined with the standard CPMG measurements in an inversion process that will be further explained to produce $T_2$ distributions.

Assuming $\vec{g}_1$ is a long wait time CPMG measurement and $\vec{g}_2$ is the average of a plurality of short wait time measurements, the following equations have to be satisfied for the underlying $T_2$ distribution, $\vec{a}$:

$$\vec{g}_1 = M_1\vec{a}$$
$$\vec{g}_2 = M_2\vec{a} \quad (9)$$

where $M_1$ and $M_2$ are the matrices according to equation (5) for the two different sets of parameters used to acquire $\vec{g}_1$ and $\vec{g}_2$ measurements. The underlying $T_2$ distribution, $\vec{a}$, is a characteristics of the sample (e.g., earth formations) and should not be affected by how the NMR measurements are acquired. Therefore, the $T_2$ distribution, $\vec{a}$, should be identical in each of the equations shown above.

Because $\vec{g}_1$ and $\vec{g}_2$ are each acquired with a different extent of stacking (signal averaging), their respective noise levels should have different standard deviations, σ1 and σ2. Taking this into account, the $T_2$ distribution, $\vec{a}$, can be determined as the minimum of the following function:

$$F(\vec{a}) = \frac{\|M_1\vec{a} - \vec{g}_1\|^2}{\sigma_1^2} + \frac{\|M_2\vec{a} - \vec{g}_2\|^2}{\sigma_2^2} + \lambda\|\vec{a}\|^2 \quad (10)$$

This equation is equivalent to equation (8), except that the weighting factors $1/\sigma_1$ and $1/\sigma_2$ are introduced in equation (10) to account for the different standard deviations of the noise in the two measurements. As stated above, the solution for the $T_2$ distribution, $\vec{a}$, can also be found as the (least squares) solution of the following matrix equation:

$$\begin{pmatrix} w_1\vec{g}_1 \\ w_2\vec{g}_2 \end{pmatrix} = \begin{pmatrix} w_1 M_1 \\ w_2 M_2 \end{pmatrix}\vec{a} \quad (11)$$

where $w_1 = 1/\sigma_1$ and $w_2 = 1/\sigma_2$. If the modified vector is defined as $$\vec{\tilde{g}} = \begin{pmatrix} w_1\vec{g}_1 \\ w_2\vec{g}_2 \end{pmatrix}$$

and matrix defined as $$\tilde{M} = \begin{pmatrix} w_1 M_1 \\ w_2 M_2 \end{pmatrix},$$

equation (11) can be written as:

$$\vec{\tilde{g}} = \tilde{M}\vec{a} \quad (12)$$

with the following (regularized, but unconstrained) solution:

$$\vec{a} = (\tilde{M}'\tilde{M} + \lambda I)^{-1}\tilde{M}'\vec{\tilde{g}} \quad (13)$$

The solution for the $T_2$ distribution, $\vec{a}$, as shown in equation (13), is the best solution to equation (10) in the least squares sense (i.e., best least square fit). However, this solution relies heavily on the precise knowledge of the matrix $\vec{M}$, which includes the polarization correction terms for both $\vec{g}_1$ and $\vec{g}_2$ measurements. The polarization correction for $\vec{g}_1$ is usually negligible except for very long $T_2$ components (which typically have very long $T_1$'s because $T_2 \leq T_1$). This is because $\vec{g}_1$ is acquired with relatively long wait time ($t_w$ in FIG. 4A) that permits most nuclear magnetizations to be fully polarized by the static magnetic field. Incomplete polarization of very long $T_2$ components may be corrected by polarization correction, which may be based on an assumption of a relationship $T_1 = f(T_2)$, or by increasing the wait time in $\vec{g}_1$ measurements so that polarization correction is really negligible even for the slowest relaxing components (over polarization).

On the other hand, polarization correction for $\vec{g}_2$ is not negligible for a wide range of $T_2$ components because $\vec{g}_2$ measurements use short wait times ($t_w$ in FIG. 4A). The solution for $T_2$ distribution, $\vec{a}$, as shown in equation (13), therefore, will strongly depend on the polarization correction term for $\vec{g}_2$.

Several approaches have been developed for polarization correction. These approaches can be classified into two categories: (a) those that suppress information in the short wait time measurements (burst measurements, $\vec{g}_2$) that is contributed by $T_2$ components with non-negligible polarization corrections; and (b) those that use two different measurements to model the $T_1 = f(T_2)$ function for polarization correction.

Methods in the first group try to restrict the influence of the burst data ($\vec{g}_2$) in the common inversion to very short $T_2$ components whose polarization correction can be ignored. In other words, the burst data are used only to complement standard CPMG data, which typically do not include reliable information on the short $T_2$ components. In one of these approaches, two measurements $\vec{g}_1$ and $\vec{g}_2$ are separately inverted and then two independent solutions are combined (spliced) to produce a common $T_2$ distribution. For example, U.S. Pat. No. 6,005,389 issued to Prammer (the Prammer patent) discloses one such method. In order to accomplish a smooth combination of two $T_2$ distribution solutions into a common one, the discrete $T_2$ values used in the two independent inversions should overlap (at the long $T_2$ end for $\vec{g}_2$ and at the short $T_2$ end for $\vec{g}_1$). Although this method seems straightforward, the accuracy of the common $T_2$ distribution that results from combining two $T_2$ distributions is questionable. This is because regularization, which unavoidably smears out the T2 distribution, affects the two independent inversions to a different extent. As a result, even though identical and overlapping $T_2$ values are chosen for the inversions, sensitivities of the two independent inversions to regularization are not necessarily identical. This can lead to artifacts in the $T_2$ distribution near the splicing point.

Another method described in the Prammer patent tries to correct incomplete polarization in the burst measurements ($\vec{g}_2$) using early echo information in $\vec{g}_1$. The first few echoes in $\vec{g}_1$, that have been acquired at the same time points (from the time of the excitation pulse) as the corresponding echoes in $\vec{g}_2$, typically reflect the fully polarized signal because the longer wait time used in $\vec{g}_1$ acquisition permits the spins (nuclear magnetizations) to relax more fully. However, these echoes exhibit more noise than the echoes in $\vec{g}_2$, because they are not as often repeated. Therefore, the average of the first few echoes in $\vec{g}_1$ (that are acquired at the same time as the echoes of $\vec{g}_2$), which is statistically more stable, is used to boost the amplitudes of the echoes for longer $T_2$ components in the $\vec{g}_2$ measurements to that which would occur if they were completely polarized. Then, a combined echo vector is inverted as outlined above, with no polarization correction for $\vec{g}_2$. This approach assumes that the average of the short wait time echoes and of the early long wait time echoes should be the same except for the insufficient polarization of the short wait time measurements. In some situations, this scheme works fairly well in correcting the non-negligible effect of incomplete polarization of the relatively long $T_2$ components in the short wait time measurements $\vec{g}_2$. However, other characteristics (not just the average) of the short wait time echoes may also be influenced by the insufficient wait time. These other characteristics are not corrected by this method.

With the second type of methods, an assumption is made about the function $T_1 = f(T_2)$ rather than just assuming that for very fast $T_2$ components, $T_1$ will be short enough to make the polarization correction negligible for $\vec{g}_2$. The usual approach is to assume $T_1 = \xi T_2$, where the ratio, $\xi$, is constant over the entire range of $T_2$ values, see for instance Dunn, K. J., Bergman, D. J., LaTorraca, G. A., Stonard, S. M., and Crowe, M. B.: "A method for inverting NMR data sets with different signal to noise ratios," paper JJ presented at the 1998 SPWLA 39th Annual Logging Symposium, Keystone, Colo., USA, May 26–29. However, the assumption of a constant $T_1/T_2$ ratio for the entire range of $T_2$ values might not be correct. Furthermore, the accuracy of the results from this approach will depend on the accuracy of the assumed $T_1/T_2$ ratio, $\xi$.

For example, FIG. 8, which will be discussed in more detail below, shows the sensitivity response curves for three dual wait time inversions using three different assumed values of $T_1/T_2$ ratio in the inversion, i.e., $\xi = 1.0$, 1.5, or 3.0 (curves 1, 2, are 3, respectively in FIG. 8), whereas the data where simulated with a $T_1/T_2$ ratio of 1.5. The sensitivity response curve is defined as the amount of porosity the inversion (including regularization) recovers at any given $T_2$. For comparison, results from an inversion of single long wait time data is also included. It is apparent from FIG. 8 that for short $T_2$ (i.e., <5 ms) components, all three dual wait time inversions produce consistent results, which are more reliable than that from the single wait time inversion. However, for components with $T_2 > 5$ ms, the three dual wait time inversions produce different results, i.e., the $T_2$ distributions in this range are highly sensitive to the value of the $T_1/T_2$ ratio, $\xi$, used. The dual wait time inversion with $\xi = 1.5$ produces a response that overlaps with the response from the single wait time inversion, suggesting that $\xi = 1.5$ is a proper value for the polarization correction in the dual wait time inversion. In contrast, results from dual wait time inversions using $\xi = 1.0$ and 3.0 deviate significantly from that from the single wait time inversion and from the ideal value of 1.0.

One way to avoid problems associated with a wrongly assumed value for the $T_1/T_2$ ratio, $\xi$, is not to assume one. British Patent No. 2,338,068 A1 issued to Freedman discloses a method to estimate the $T_1/T_2$ ratio together with the $T_2$ distribution, $\vec{a}$, by minimizing a function like that shown in equation (10) with respect to $\vec{a}$ and $\xi$, i.e., $$F(\vec{a}, \xi) = \frac{\|M_1(\xi)\vec{a} - \vec{g}_1\|^2}{\sigma_1^2} + \frac{\|M_2(\xi)\vec{a} - \vec{g}_2\|^2}{\sigma_2^2} + \lambda\|\vec{a}\|^2 \quad (14)$$

where the matrices $M_1$ and $M_2$ depend on $\xi$ via their respective polarization correction terms. The minimization of cost function (14) is no longer a linear problem. Thus, the minimization of cost function (14) is numerically more challenging than the minimization of equation (10). Furthermore, the additional parameter ($\xi$) to minimize in cost function (14) causes the problem to be less stable than the standard minimization of the function shown in equation (10).

A comparison between the first category of methods and the second category of methods suggests that the first type of method may be a better approach. Methods in the first category suppress information of $T_2$ components that are not fully polarized (i.e., polarization correction is necessary) by the short wait time used in the acquisition of $\vec{g}_2$. In other words, these methods try to use only information from $T_2$ components in $\vec{g}_2$ that are fully polarized (i.e., short $T_2$ components). As stated above, the methods known in the art try to accomplish this by modifying $\vec{g}_2$ using information computed from $\vec{g}_1$.

Embodiments of the present invention accomplish using information only from $\vec{g}_2$ by forming linear combinations of echoes from $\vec{g}_2$ to produce a "modified" burst data set that depends only on very fast $T_2$ components. Therefore, polarization correction is unnecessary with the "modified" burst data. These linear combinations (the modified burst data), instead of the original echoes in $\vec{g}_2$, can then be used in the common inversion to derive the $T_2$ distributions.

As stated above, the goal of a common inversion of two data sets $\vec{g}_1$ and $\vec{g}e_2$ is to compute the least squares solution of:

$$\vec{g}_1 = M_1 \vec{a}$$

$$\vec{g}_2 = M_2 \vec{a} \quad (15)$$

In embodiments of the present invention, modified burst data, which are linear combinations of echoes in $\vec{g}_2$ that only depend on $T_2$ components with negligible polarization correction, are used in the common inversion. These linear combinations of echoes will be referred to as a "modified burst measurement." Therefore, in embodiments of the invention, the goal of a common inversion is to compute the least squares solution of:

$$\vec{g}_1 = M_1 \vec{a}$$

$$X\vec{g}_2 = XM_2\vec{a} \quad (16)$$

where X is a matrix that accomplishes the desired linear combination of echoes in $\vec{g}_2$. The matrix X (or X $M_2$) will be described in more detail later. Equation (16) has the exact same form as that of equation (9). Therefore, the unconstrained and regularized solution for the $T_2$ distribution, $\vec{a}$, can be likewise defined as:

$$\vec{a} = (\tilde{M}^T \tilde{X}^T \tilde{X} \tilde{M} + \lambda I)^{-1} \tilde{M}^T \tilde{X}^T \tilde{X} \vec{g} \quad (17)$$

Similarly, the solution for the $T_2$ distribution, $\vec{a}$, may be obtained from a constrained minimization of the following cost function:

$$F(\vec{a}) = \frac{\|M_1\vec{a} - \vec{g}_1\|^2}{\sigma_1^2} + \frac{\|XM_2\vec{a} - X\vec{g}_2\|^2}{\sigma_2^2} + \lambda\|\vec{a}\|^2 \quad (18)$$

$$= \left\|\tilde{X}\tilde{M}\vec{a} - \tilde{X}\vec{\tilde{g}}\right\|^2 + \lambda\|\vec{a}\|^2$$

where $$\tilde{X} = \begin{pmatrix} 1 & 0 & \cdots & 0 & 0 \\ 0 & 1 & \cdots & 0 & 0 \\ \vdots & \vdots & \ddots & \vdots & \vdots \\ 0 & 0 & \cdots & 1 & 0 \\ 0 & 0 & \cdots & 0 & X \end{pmatrix}, \vec{\tilde{g}} = \begin{pmatrix} w_1\vec{g}_1 \\ w_1\vec{g}_2 \end{pmatrix}, \tilde{M} = \begin{pmatrix} w_1 M_1 \\ w_2 M_2 \end{pmatrix} \quad (19)$$

and $w_1 = 1/\sigma_1$ and $w_2 = 1/\sigma_2$.

The matrix X in equation (16) is determined so that the resultant linear combinations of echoes of $\vec{g}_2$ are not sensitive to $T_2$ components that require polarization correction, i.e., those $T_2$ components that require polarization correction are suppressed (or removed). To accomplish this, the X $M_2$ matrix in equation (16) should contain rows of zero vectors beyond a certain row. Assuming that $T_1 = f(T_2)$ is a monotonic function and that polarization correction of $\vec{g}_2$ is negligible for echoes with $T_1$ values smaller than a cutoff value $T_1^0$, i.e., $T_0 \leq T_1^0$, or for echoes with $T_2$ values smaller than a cutoff value $T_2^0$, i.e., $T_2 \leq T_2^0 = f^{-1}(T_1^0)$, then X $M_2$ can be written as a new matrix M' as shown in the following equation:

$$XM_2 = M' = \begin{pmatrix} x & x & \cdots & x \\ \vdots & \vdots & \ddots & \vdots \\ x & x & \cdots & x \\ 0 & 0 & \cdots & 0 \\ \vdots & \vdots & \ddots & \vdots \\ 0 & 0 & \cdots & 0 \end{pmatrix} \leftarrow j_0^{th} \text{ row} \quad (20)$$

where $j_0^{th}$ row indicates the row with the cutoff $T_2^0$ value, i.e., $T_{2j_0} \leq T_2^0$. Rows before the $j_0^{th}$ row would have their $T_2$ values smaller than the cutoff $T_2^0$ value, whereas those beyond the $j_0^{th}$ row have their $T_2$ values greater than the cutoff $T_2^0$ value, i.e., $T_{2(j_0+1)} \geq T_2^0$. The matrix M' shown in equation (20) suppresses contributions from echoes beyond the $j_0^{th}$ row. The x in the above matrix simply denotes that it is a number; however, it does not mean that all x's in the above matrix have identical values. In other words, the "x" in the matrix should be $x_{ij}$, where i and j, row and column numbers, are omitted for clarity of the above formula. Note that the number of rows of X is not predetermined. The row vectors of X describe the linear combinations of echoes in $\vec{g}_2$. The number of linear combinations to be used should be determined based on how many independent linear combinations that fulfill the above stated requirement are possible. Note further that each j-th column in matrix $M_2$ describes a mono exponential decay of a spin with amplitude 1.0 and relaxation time $T_{2j}$. Therefore, the above given condition means nothing more than that the linear combinations described by X have to be zero for spins with $T_2 \geq T_2^0$. In other words, $T_2$ components whose polarization correction might not be negligible should not contribute to the linear combinations. Thus, the search for a proper X for this purpose relates to the search for the null space of $M_2^{(j_0)}$, where $M_2^{(j_0)}$ is the lower part of the matrix $M_2'$; starting from the $j_0^{th}$ row A null space of $M_2^{(j_0)}$ is the set comprising all vectors, $\vec{x}_k$, which are solutions to the following system of equations:

$$M_2^{(j_0)}\vec{x}_k = \vec{0} \qquad (21)$$

The system of equation (21) has a trivial, particular solution $\vec{x}_k = \vec{0}$. The general solution for the under determined system of equation (21) includes the particular solution, $\vec{x}_k = \vec{0}$, and any linear combination of the basis vectors of the null space of $M_2^{(j_0)}$. To find a system of basis vectors for the null space of $M_2^{(j_0)}$, the singular value decomposition of $M_2^{(j_0)}$ is used:

$M_2^{(j_0)} = U\,S\,V'$, where U and V are orthogonal, i.e., V V'=V' V=I, U' U=I, I is an identity matrix, and S is a diagonal matrix having the following form:

$$S = \begin{pmatrix} s_1 & 0 & \cdots & 0 \\ 0 & s_2 & \cdots & 0 \\ \vdots & \vdots & \ddots & \vdots \\ 0 & 0 & \cdots & s_n \end{pmatrix} \text{ with } s_1 \geq s_2 \geq \ldots \geq s_n \geq 0 \qquad (22)$$

The diagonal elements of S (i.e., $S_1, S_2, \ldots, S_n$) are the singular values of $M_2^{(j_0)}$. One skilled in the art would know how to perform the singular value decomposition of a matrix, and there are commercially available programs for this purpose. Furthermore, U.S. Pat. No. 5,363,041 issued to Sezginer also discloses procedures for singular value decomposition in a data compression scheme. This patent is assigned to the same assignee as the present invention and is hereby incorporated by reference.

Figure 5:
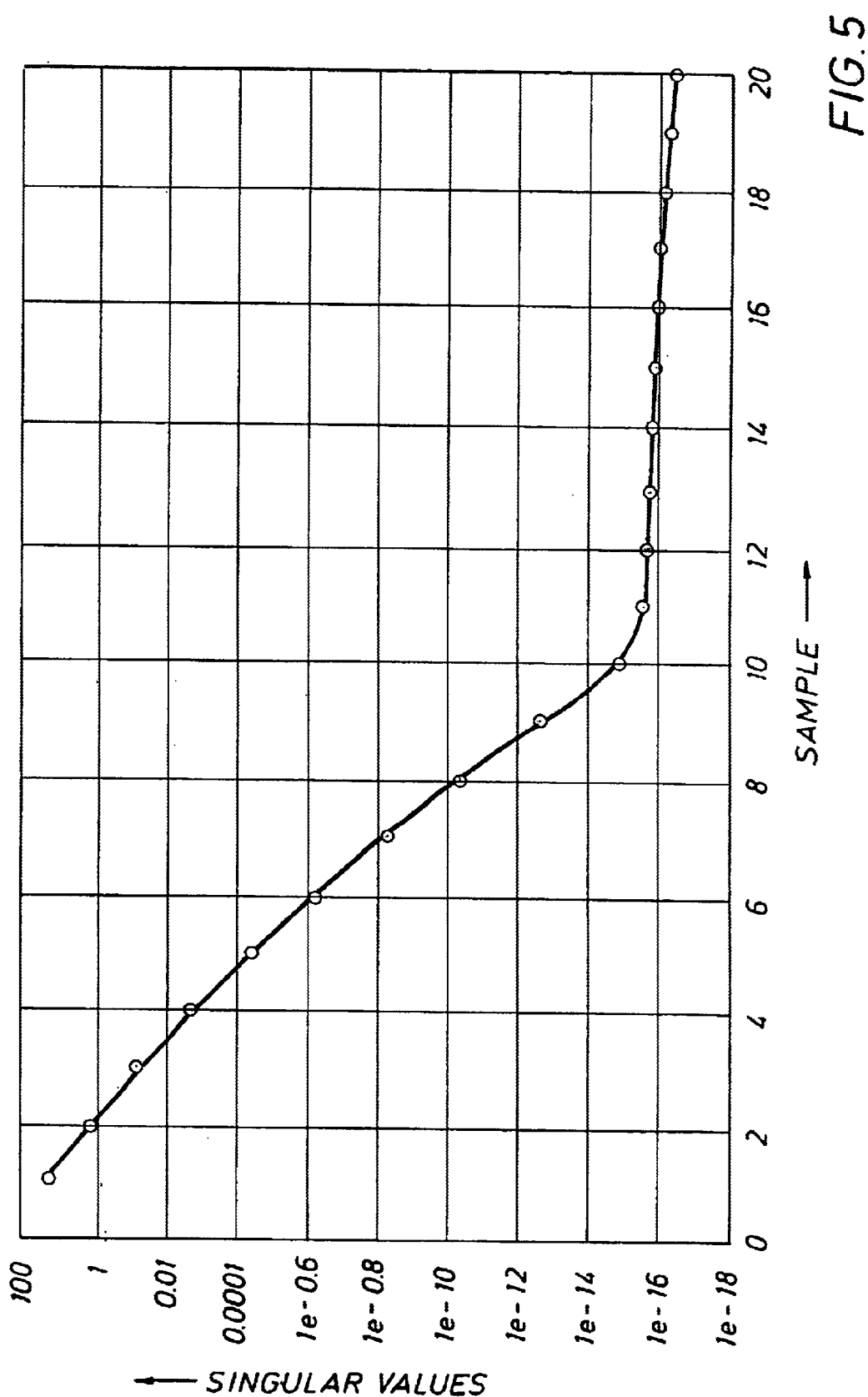
FIG. 5 is a logarithmic plot of the singular values of matrix $M_2^{(j_0)}$ for a typical set of acquisition parameters.

From the singular value decomposition, the null space of $M_2^{(j_0)}$ may be constructed of the column vectors of V that belong to the zero singular values. To do this, one first finds the number of non-zero singular values of $M_2^{(j_0)}$, say r (which is known in the art as the "rank" of matrix $M_2^{(j_0)}$). Then, the (r+1)-th and higher column vectors of V would constitute the null space of $M_2^{(j_0)}$). In practice, however, there are no singular values of $M_2^{(j_0)}$ that are true zero, because matrix $M_2$ describes exponential decays of nuclear magnetizations. For example, FIG. 5 shows a logarithmic plot of the singular values of $M_2^{(j_0)}$ for a typical set of acquisition parameters. It is apparent from FIG. 5 that the singular vales of $M_2^{(j_0)}$) decrease rapidly to very small values, but they never really become zero. Therefore, no linear combination of the burst echoes can completely avoid the influence of the longer $T_2$ components. However, the singular values of $M_2^{(j_0)}$ typically decay rapidly (see FIG. 5). Consequently, the singular values of $M_2^{(j_0)}$ from some point on (e.g., the fourth one) would have diminished to a value that is negligibly small (i.e., practically zero) for the purpose of the invention. It is apparent from FIG. 5 that the singular values decay rapidly, and the fourth value (about 0.001) is already considerably smaller than the first one (about 10). Thus, the singular values of $M_2^{(j_0)}$, in this example, from the fourth one on are practically zero, and the null space of $M_2^{(j_0)}$, therefore, will comprise the fourth and higher column vectors of V.

Figure 6:
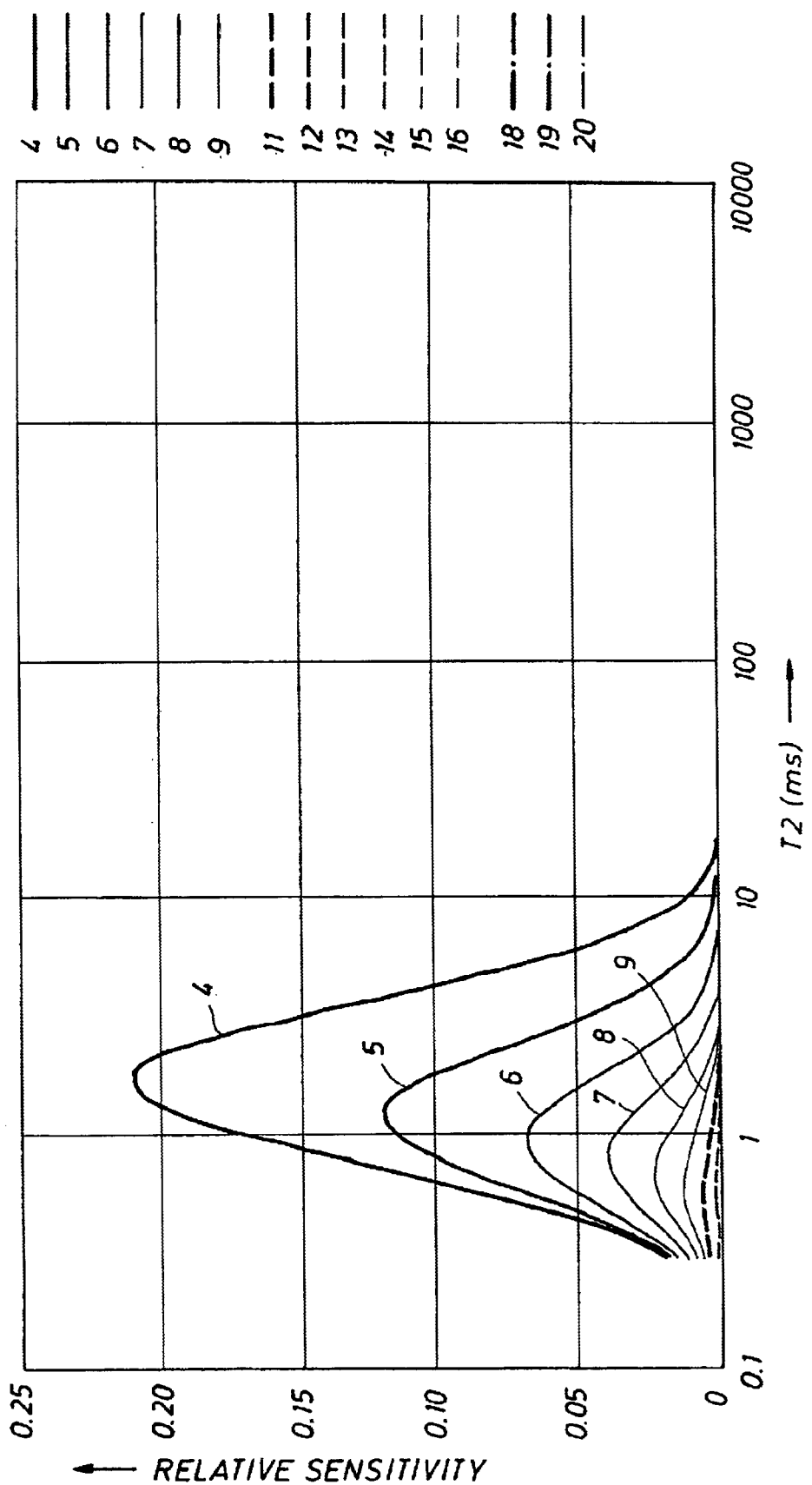

To show that the null space of $M_2^{j_0}$ can be used to suppress the $T_2$ components that have non-negligible polarization correction, one would compare the sensitivities of various $T_2$ components after such operation. Sensitivities of the linear combinations of the burst echoes with respect to $T_2$ may be computed from the scalar product of a row vector of X with each column vector of $M_2$ (see equation (16)). FIG. 6 shows the sensitivities for each column vector of matrix V computed using the singular values from the fourth singular value onwards. It is apparent that the higher the order of the singular value is, the smaller the sensitivity gets and the better it is confined to the fast $T_2$ components. Even the sensitivity for the fourth singular value is already reasonably well confined below 10 ms, which was used as cut-off $T_2$ value in this example. This example clearly demonstrates that the approach described herein can produce linear combinations that are only sensitive to short $T_2$ components (<10 ms). Thus, the fourth and higher column vectors of V can indeed be regarded as the "null space" of $M_2^{(j_0)}$ for the purpose of linear combinations described herein.

The above describes linear combinations via matrix operations that make use of null space matrices. While this is a convenient procedure, other methods that can achieve the same effects as these linear combinations may also be used. Any set of functions of the burst echoes $g_2$ that fulfill the requirement not to be sensitive to $T_2$ values with non negligible polarization correction in the bursts can be used for the above described inversion. Such functions will be generally referred to as "suppression functions." The purpose of the suppression functions is to suppress the contribution from $T_2$ components whose polarization correction is not negligible. Such "suppression functions" may be linear combination functions as described above or some other functions (whether linear or non-linear).

Figure 7:
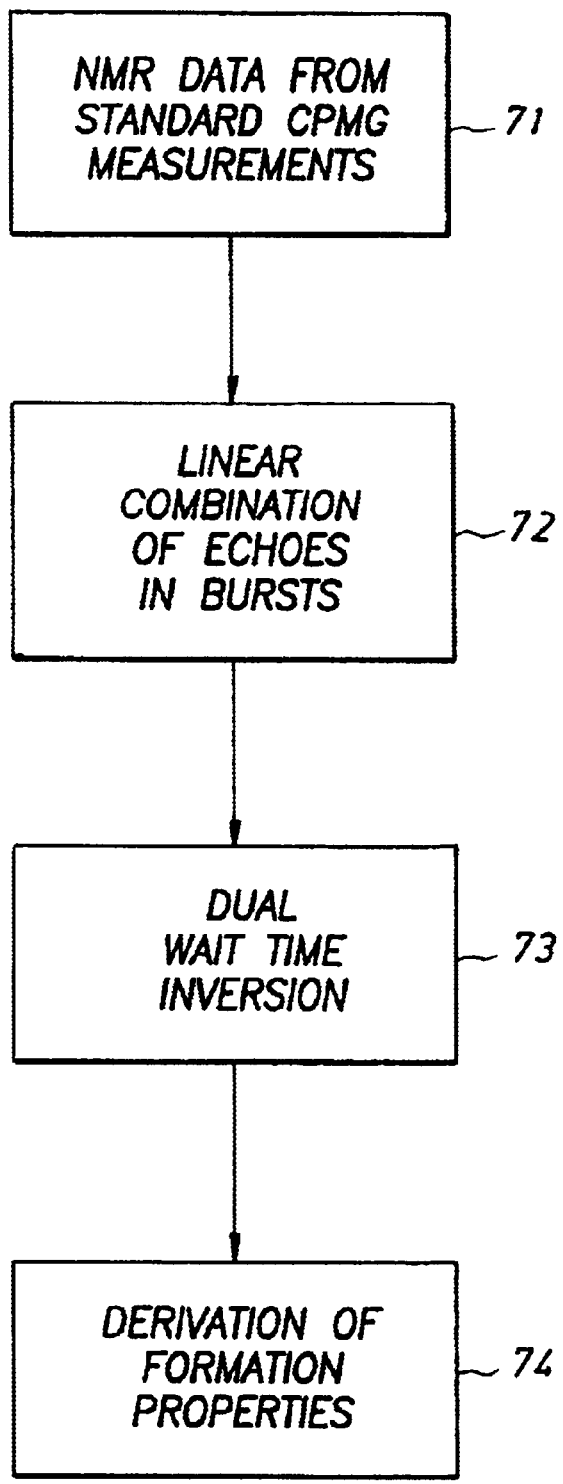
FIG. 7 is a schematic of processes involved in a method according to one embodiment of the invention.

FIG. 7 shows a schematic of a method according to embodiments of the invention. First, NMR data are acquired (as shown at 71). The NMR data should include at least one measurement set from a standard spin echo (e.g., CPMG) sequence ("standard CPMG measurement set" or "standard spin echo measurement set") and at least one measurement set from a burst measurement sequence ("burst measurement set"). Dual wait time measurements are well known in the art. The burst measurements sets are typically acquired with repeated, short wait time spin echo (e.g., CPMG) sequences. The short wait times ($t_w$) in the repeated, short wait time CPMG sequences are typically less than 1 second (more typically in the ranges of tens to hundreds of milliseconds). In contrast, the wait time for a standard CPMG sequence may be in the range of several seconds (e.g., 1–5 s). A "standard CPMG measurement" as known in the art typically uses a wait time so that most of the nuclear spins of interest would be substantially polarized by the static magnetic field. Although it is generally believed that five times the $T_1$ relaxation is required for full polarization, it is possible to use a slightly shorter wait time to optimize the use of the measurement time. A standard CPMG sequence may collect many hundreds to a couple thousands of echoes (typically 400–1000 echoes), while the burst sequence typically collects from a few dozens to a few hundreds echoes (typically 100–400 echoes). Typical inter-echo delay in a standard CPMG measurement may be from a few tenths of a millisecond to a few milliseconds.

A burst sequence takes much less time than does a standard CPMG sequence and is often repeated to allow stacking (averaging) of the collected signals to improve the signal to noise ratio. Thus, the burst measurements may be acquired by repeating the short wait time CPMG sequences from several times to several dozen times, depending on the desired signal stacking (averaging). U.S. Pat. No. 6,331,775 issued to Them et al., and U.S. Pat. No. 6,005,389 issued to Prammer disclose examples of dual wait time CPMG measurements that may be used to practice the present invention. It is preferred that the inter-echo delays ($t_e$) are the same between the standard CPMG sequence and the burst sequences so that data inversion is simpler. However, the inter-echo delays may also be different between the standard CPMG experiment and the burst experiment. See U.S. Pat. No. 6,377,042 B1 issued to Menger et al., for example, for a method of inverting data sets with different inter-echo delays. The precise parameters (e.g., wait time, number of echoes, and inter-echo delays) will depend on the properties of the samples under investigation. One skilled in the art would know how to optimize these parameters for a particular sample.

While CPMG is the most common pulse sequence for well logging, one skilled in the art would appreciate that any method known in the art for spin echo measurements may be used without departing from the scope of the invention. For example, the original Carr-Purcell pulse sequence without the modification by Meiboom and Gill may be used. In addition, spin lock may be used instead of a train of inversion (refocusing, 180-degree) pulses for the investigation of $T_2$ relaxation process. Likewise, repeated Hahn spin echo pulse sequence, which is tantamount to a single echo CPMG sequence, may be used. All these pulse sequences that permit measurements of spin echoes will be referred to as "spin echo pulse sequences," while those used for short wait time (burst) measurements will be referred to as "short wait time spin echo pulse sequences." Note that the same type of spin echo pulse sequence should be used for both the standard spin echo measurement and the burst measurement. In addition, one skilled in the art would appreciate that these pulse sequences may be used in the "phase alternating" mode, in which the excitation 90-degree pulse is phase-shifted by 180 degrees (from X-axis to −X-axis) in alternating acquisitions, and the data from the alternating measurements are subtracted to produce better quality data.

Any pulse sequence arrangements known in the art may be used for the NMR measurements. For example, U.S. Pat. No. 6,005,389 issued to Prammer discloses an arrangement in which a standard CPMG pulse sequence is followed by short burst sequences that are repeated several times. With this pulse sequence arrangement, the long wait time standard CPMG measurement and the short wait time burst measurements may be acquired in a single logging operation. Alternatively, the standard CPMG measurements and the burst measurements may be acquired separately, e.g., in separate logging operations or in separate runs. In yet another alternative, the standard CPMG measurements (fully polarized) and the burst measurements may be acquired "semi-simultaneously" using dual-volume tools such as that sold under the trade name of MRIL™ by NUMAR Corporation (Malvern, Pa.). In addition, these NMR measurements may be performed in a borehole that penetrates the earth formations, or on a core sample that had been removed from the formations. The formations and the core samples will be generally referred to as earth formation samples. Note that "an earth formation sample" may include two or more adjacent volumes under investigation (areas of interest or areas of investigation) using a dual-volume type tools. The logging operation may be performed with a wireline tool or a measurement while drilling (MWD or LWD) tool.

In embodiments of the invention, suppression functions will then be applied to the spin echoes in the burst measurements to suppress contributions of $T_2$ components whose polarization corrections are not negligible (shown at 72). The suppression functions may be linear combination functions as shown above or any other functions (linear or not) that can achieve the suppression of the contributions of $T_2$ components whose polarization corrections are not negligible. The suppression functions (e.g., linear combination functions) may be a null space of a matrix that describes the exponential decays of the nuclear spins according to the acquisition parameters as described above. The null space may be derived from singular value decomposition of the matrix as shown above. The burst data after such combinations will contain $T_2$ components whose polarization correction may be ignored.

The burst data (NMR measurements from burst experiments) after the operation with the suppression functions (e.g., linear combinations) yield a modified burst data set. The modified burst data set is then used in a common inversion together with the data from the standard CPMG sequence (shown at 73) to produce a distribution of an NMR parameter (e.g., $T_2$). The NMR parameter may be $T_1$, $T_2$, $T_1/T_2$, or diffusion constant (D). Note that for a measurement of $T_1$ or $T_1/T_2$ the polarization correction is used to compute these values. However, the invention can still be practiced to restrict the influence of the polarization correction to a desirable range. For clarity, the following discussion will assume the NMR parameter is $T_2$. Although the two data sets may be independently inverted and the resultant $T_2$ distributions spliced to give a $T_2$ distribution solution, it is preferred that both data sets are inverted in a common inversion process so as to avoid the problems associated with splicing two independently derived $T_2$ distributions. The inversion process, as used herein, takes the two data sets (the modified burst data set and the standard CPMG measurement set) as an input and produces $T_2$ distributions as an output. The inversion process, as can be seen from equation (16), involves applying the same suppression functions X to the forward model $M_2 \vec{a}$, where matrix $M_2$ describes the exponential decays of echoes according to the acquisition parameters of the burst measurement. Thus, contribution of $T_2$ components whose polarization correction is non-negligible is suppressed in both the measurement data (left hand side of the equation, $\vec{g}_2$) and the forward model (right hand side of the equation, $M_2 \vec{a}$). The output $T_2$ distributions, $\vec{a}$, may then be obtained as solutions to equation (17), which, as stated above, may be obtained by minimizing a cost function as shown in equation (18). The solution to the new inversion scheme according to the invention, like the inversion of standard CPMG measurements, is a linear problem. Therefore, the inversion programs already in use for single CPMG inversions can be used for this new scheme.

The inversion processes may include regularization. U.S. Pat. No. 5,363,041 issued to Sezginer discloses methods to optimize the regularization factors. This patent is assigned to the same assignee as the present invention and is hereby incorporated by reference. In addition, the inversion processes may include positivity constraint. One skilled in the art would know how to achieve the positivity constraint.

The $T_2$ distributions obtained from the inversion may then be used to compute the formation properties (shown at 74). Alternatively, formation properties (e.g., porosity) may be directly derived from the CPMG measurements and the burst data without first deriving the $T_2$ distributions. The formation properties that may be derived from the $T_2$ distribution include formation porosity, water-filled porosity, oil-filled porosity, etc. Any method known in the art may be used to compute these formation properties. For example, formation porosities ($\Phi$) may be computed from the $T_2$ distributions, $\vec{a}$, by summing up all elements of $\vec{a}$, i.e., $\Phi = \vec{e} \, \vec{a} = \vec{e} \, (M'X'XM + \lambda I)^{-1} M'X'X \, \vec{g}$. Computation of the formation porosities ($\Phi$) at each of the $T_2$ bins (i.e., each discrete $T_2$ value used in the inversion) leads to:

$$\vec{s} = \vec{e} \, (\tilde{M}'\tilde{X}'\tilde{X}\tilde{M} + \lambda I)^{-1} \tilde{M}'\tilde{X}'\tilde{X}\tilde{M} \qquad (23)$$

where $\vec{e}$ is a row vector of 1, i.e., $\vec{e} = (1 \ldots 1)$, and the vector $\vec{s}$ describes the porosity, that is to be computed from the measurements, relative to the true porosity. As such, $\vec{s}$ depends on the relaxation time $T_2$. Thus, $\vec{s}$ describes the sensitivity of the measurements with respect to $T_2$. The expression (23) is valid only for a linear inversion, i.e., without applying positivity constraint, because the sensitivity response of inversions with positivity constraint can only be determined by Monte Carlo simulations and may depend on true $T_2$ distributions. Nevertheless, results from the linear inversion may provide a good approximation for the sensitivity of an inversion with positivity constraint.

Embodiments of the present invention will now be illustrated with the following examples. FIG. 8 shows the sensitivity curves for a single wait time inversion using a long wait time CPMG measurement and for dual wait time inversions using the same long wait time CPMG measurement in combination with burst measurements. Both the single wait time inversion and the dual wait time inversions are performed with the prior art methods, instead of the inversion scheme of the present invention.

The long wait time CPMG measurement was acquired with a wait time ($t_w$) of 5 s and an inter-echo delay ($t_e$) of 1 ms for 200 echoes. The inversions were performed with regularization that was chosen so that an average of two measurements gives a porosity estimate with the same standard deviation as the single echoes. For the dual wait time inversion, a single long wait time CPMG measurement and bursts during the time for the second long wait time measurement were assumed, so that a full acquisition of the second sequence takes the same amount of time as the first scheme. The bursts were acquired with a wait time of 40 ms and same echo spacing, $t_e=1$ ms, for 20 echoes. The dual wait time inversions were performed with regularization so that the same standard deviation as that of the single wait time CPMG measurement was achieved. The inversion was done using the straight forward dual wait time inversion described above, i.e., by minimizing the function shown in equation (10). For the computation of the sensitivity curves, a fixed $T_1/T_2$ ratio $\xi$ over the full $T_2$ range was assumed. For the single wait time experiment only the curve for $\xi=1.5$ is given. The sensitivity of this curve depends on only for very long $T_2$'s. For the dual wait time inversion, sensitivities for $\xi=1.0$, $\xi=1.5$, and $\xi=3.0$ are shown in FIG. 8.

Figure 8:
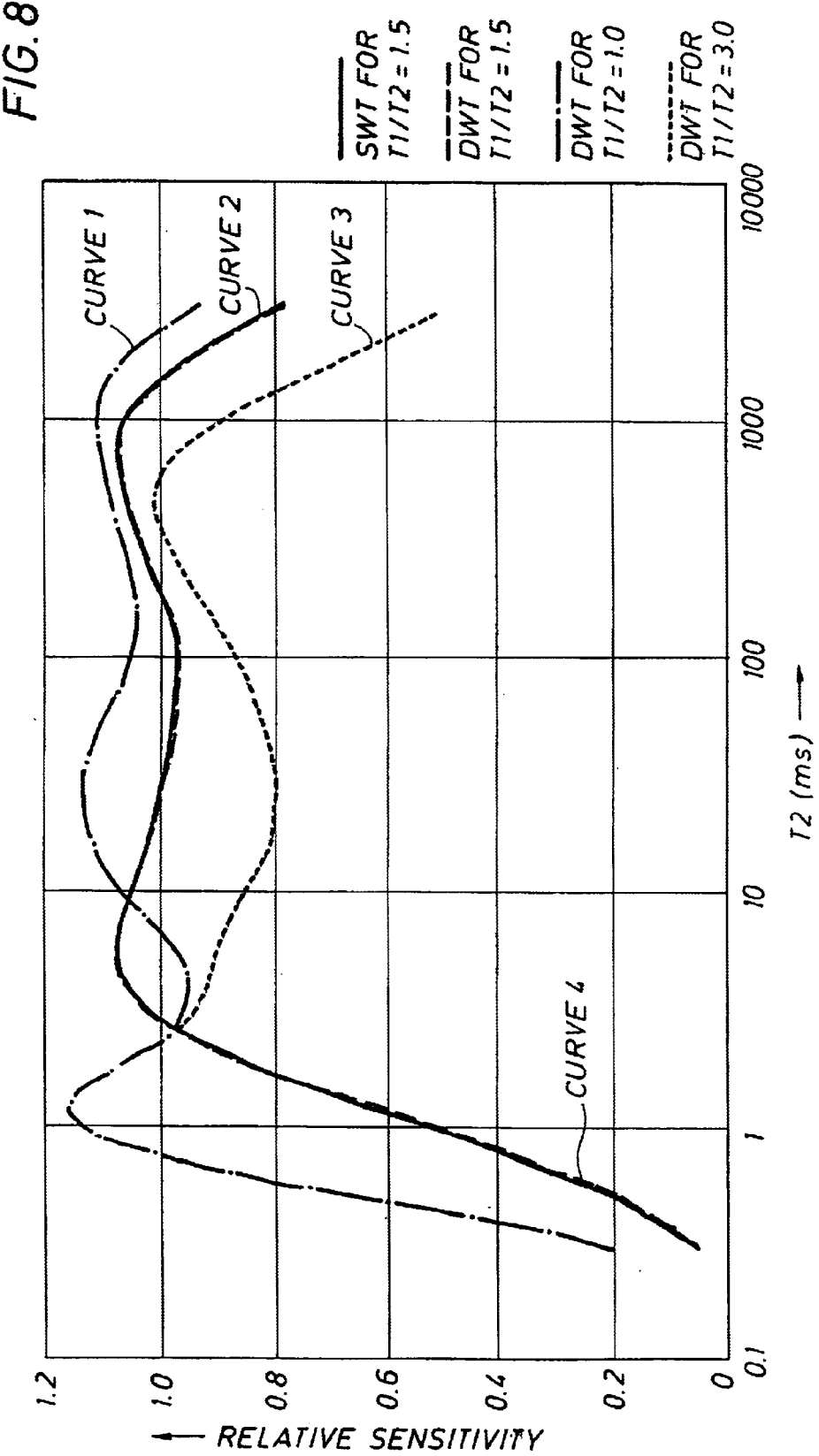
FIG. 8 is a chart illustrating sensitivity curves for a prior art dual wait time inversion.

It is apparent from FIG. 8 that the sensitivity of the dual wait time measurement extends to much shorter $T_2$ range (<3 ms; curves 1, 2, and 3) than does the single wait time measurement (curve 4). This is because the fast and often repeated burst measurements determine the fast decaying components better. In addition, in the short $T_2$ range, polarization correction is negligible and, therefore, an incorrect $T_1/T_2$ ratio used in the polarization correction would not have any appreciable effect. This is evident from the fact that the sensitivity curves from three inversions, using $\xi=1.0$, $\xi=1.5$, and $\xi=3.0$, (curves 1, 2, and 3, respectively, in FIG. 8) of the dual wait time measurement differ very little in the range of fast $T_2$ (<5 ms).

A comparison between the single wait time inversion (curve 4) and the dual wait time inversion shows that for $\xi=1.5$ (curve 2), both measurements show the same behavior for the long $T_2$ components (>5 ms). The sensitivity curves for the inversions of the dual wait time measurement using different $T_1/T_2$ ratios (curves 1, 2, and 3), however, differ significantly in the medium and long $T_2$ range (>5 ms). This is due to the fact that incomplete polarization of medium and long $T_2$ components in the burst measurements is non-negligible in this region. Thus, in this region, the polarization correction for the bursts is necessary and if the polarization correction is performed improperly (i.e., using an incorrect $T_1/T_2$ ratio, $\xi$), results from the inversion would be erroneous.

Figure 9:
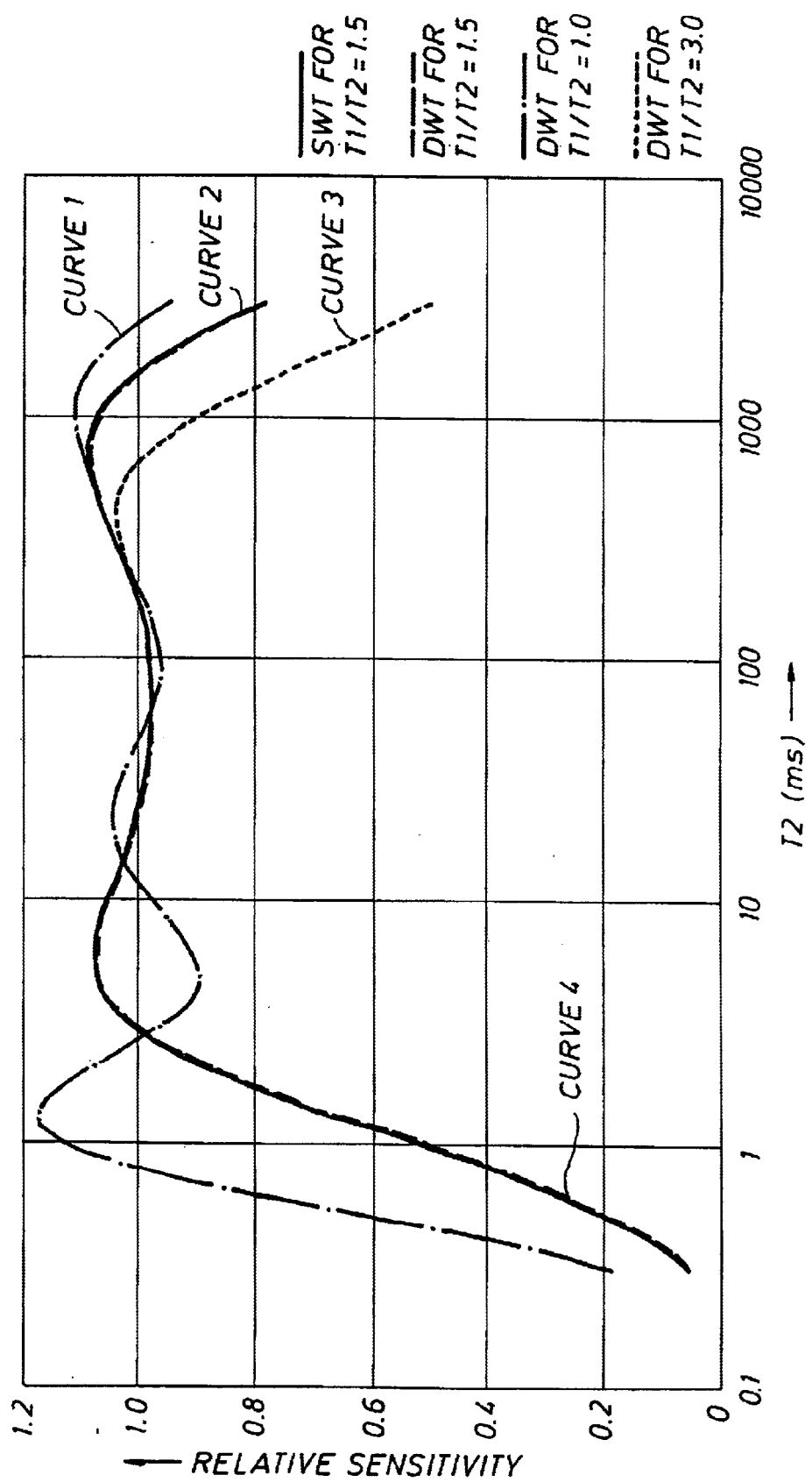
FIG. 9 is a chart illustrating sensitivity curves for a dual wait time inversion according to one embodiment of the invention.

FIG. 9 shows the sensitivity curves (curves 1, 2, and 3, respectively, for $T_1/T_2=1.0$, 1.5, and 3.0) for the dual wait time inversions using methods according to embodiments of the invention to suppress the influence of the bursts for $T_2$ components with non-negligible polarization correction. For comparison, the sensitivity of the single wait time measurement is also shown (curve 4). The dual wait time inversion sensitivities extend to fast $T_2$ components (<5 ms) better than does the single wait time inversion. This result is expected and is consistent with that shown in FIG. 8 from a prior art dual wait time inversion. With the inversion scheme according to the invention, however, the sensitivities of the dual wait time measurement with different $T_1/T_2$ ratios (curves 1, 2, and 3, respectively, for $T_1/T_2=1.0$, 1.5, and 3.0) do not differ significantly for $T_2$ values up to about 500 ms. This is a significant improvement as compared with that from the prior art dual wait time inversions as shown in FIG. 8, which shows significant variations in sensitivities for $T_2 > 5$ ms. However, the sensitivity towards faster decaying components is somewhat lower than the one for the straight forward dual wait time inversion.

Figure 10:
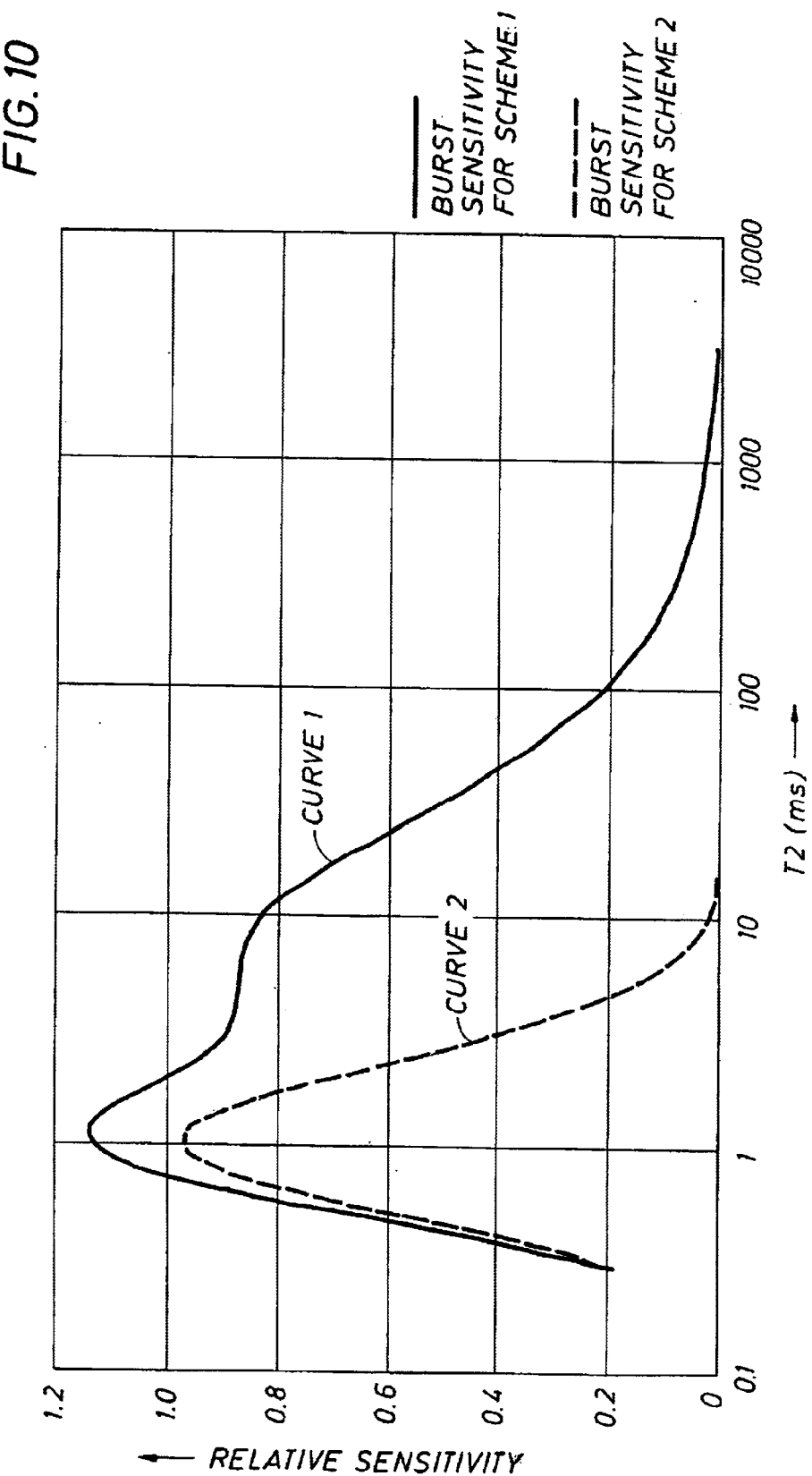
FIG. 10 is a chart illustrating sensitivity curves of the burst data for both the prior art dual wait time inversion and the dual wait time inversion according to one embodiment of the invention.

FIG. 10 shows the sensitivity for both dual wait time inversion schemes, i.e., prior art dual wait time inversion scheme (which will be referred to as Scheme 1; curve 1) and the new dual wait time inversion scheme according to embodiments of the invention (which will be referred to as Scheme 2; curve 2), with respect to the burst echoes only. It is apparent that the burst data contribute to the sensitivities of $T_2$ components up to 100 ms to a significant extent using the conventional inversion of Scheme 1 (curve 1). For those components, the polarization corrections in the burst measurements are not negligible. Therefore, incorrect polarization correction (e.g., the use of incorrect $T_1/T_2$ ratio, $\xi$) will lead to erroneous results. In contrast, an inversion method according to the invention (Scheme 2) minimizes the influence of $T_2$ components with non-negligible polarization correction (e.g., components with $T_2 > 10$ ms) in the bursts. Indeed, the influence of the bursts on $T_2$ sensitivity according to an inversion method of the invention is restricted to short $T_2$ components (e.g., below 10 ms; curve 2).

The above inversions were performed without positivity constraints. To study the performance of dual wait time inversion methods according to the invention (e.g., Scheme 2) with the positivity constraint, Monte Carlo simulations were performed on simulated echo data corresponding to the two $T_2$ distributions shown in FIGS. 11 and 15. The total porosity for both examples is 30 p.u. For the inversion, a $T_1/T_2$ ratio of 1.5 was assumed. The echoes, however, were simulated with a $T_1/T_2$ ratio of 3.0 in order to test how well the different inversion schemes cope with a wrongly assumed $T_1/T_2$ ratio. For each Monte Carlo experiment, 10000 echo trains with different noise realizations with a standard deviation of 1 p.u. were simulated and then inverted.

Figure 11:
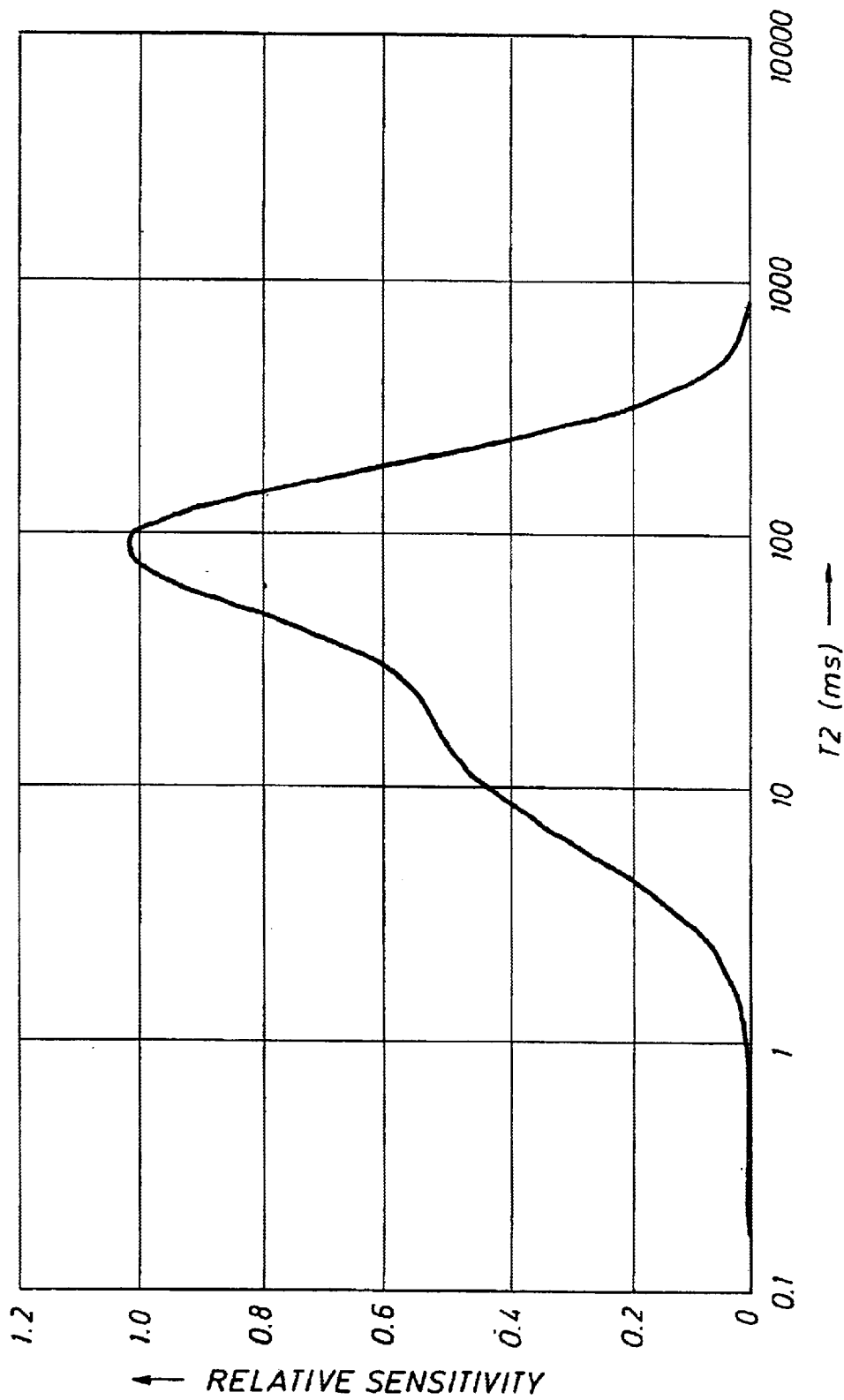
FIG. 11 is a chart showing the input $T_2$ distribution used in a first Monte Carlo simulation.
Figure 12:
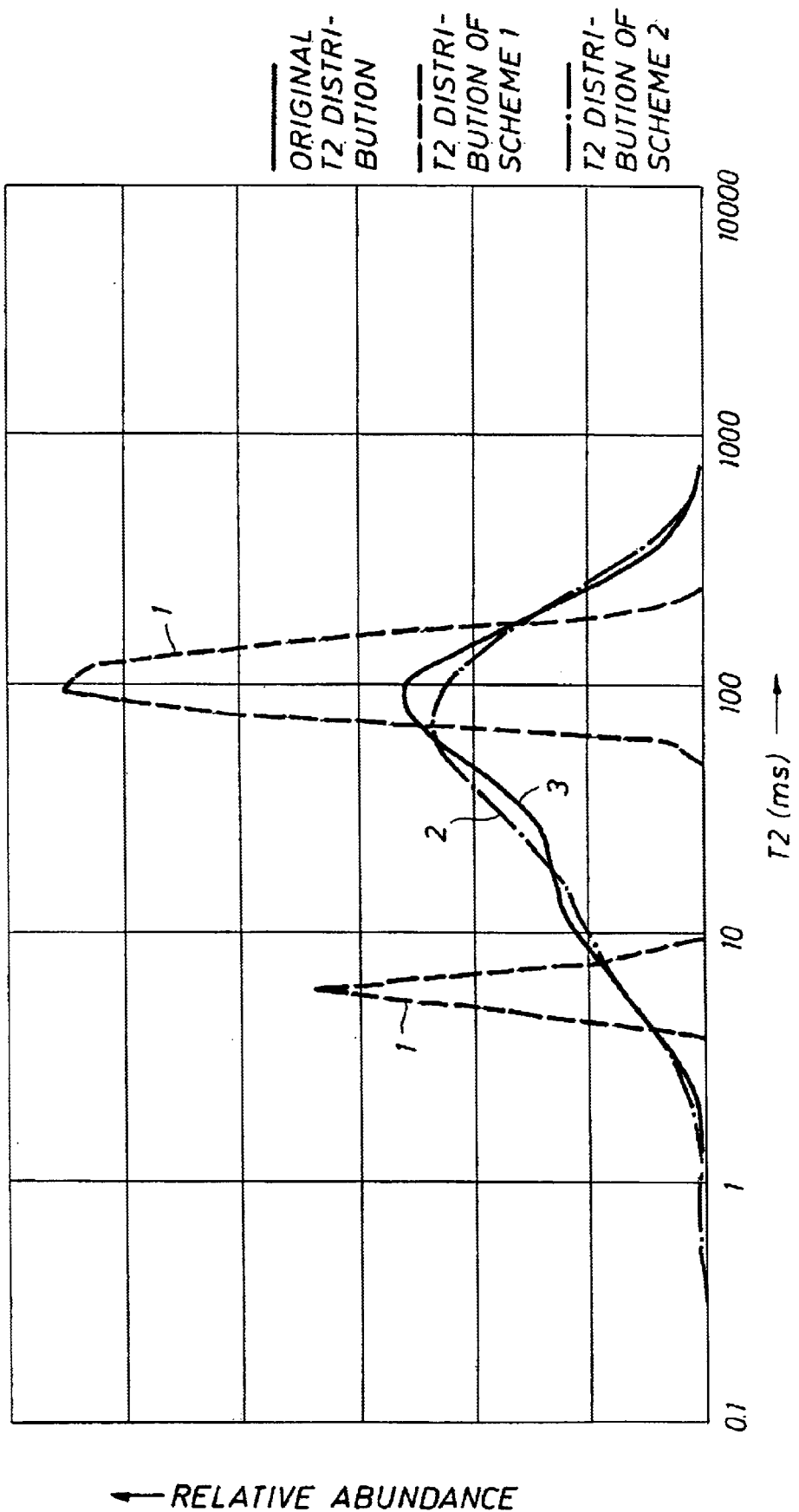
FIG. 12 is a chart illustrating the averaged $T_2$ distributions for the Monte Carlo simulations for the two inversion schemes on the $T_2$ distribution shown in FIG. 11.

FIG. 12 shows the $T_2$ distributions from the two inversions schemes using Monte Carlo simulations. For comparison, the input $T_2$ distribution (curve 3) as shown in FIG. 11 is superimposed on the results from the inversions. These inversions were performed Iwith regularization that was chosen so that the standard deviation of the equivalent porosity estimation is comparable in both inversions. It is apparent from FIG. 12 that the inversion methods according to the invention (e.g., Scheme 2; curve 2) produces a smooth $T_2$ distribution, which closely follows the input $T_2$ distribution (curve 3). In contrast, the straight forward inversion (Scheme 1; curve 1) produces artificially narrow $T_2$ distributions, which comprise two discrete populations of $T_2$ components that are very different from the input $T_2$ distributions (curve 3).

Figure 13:
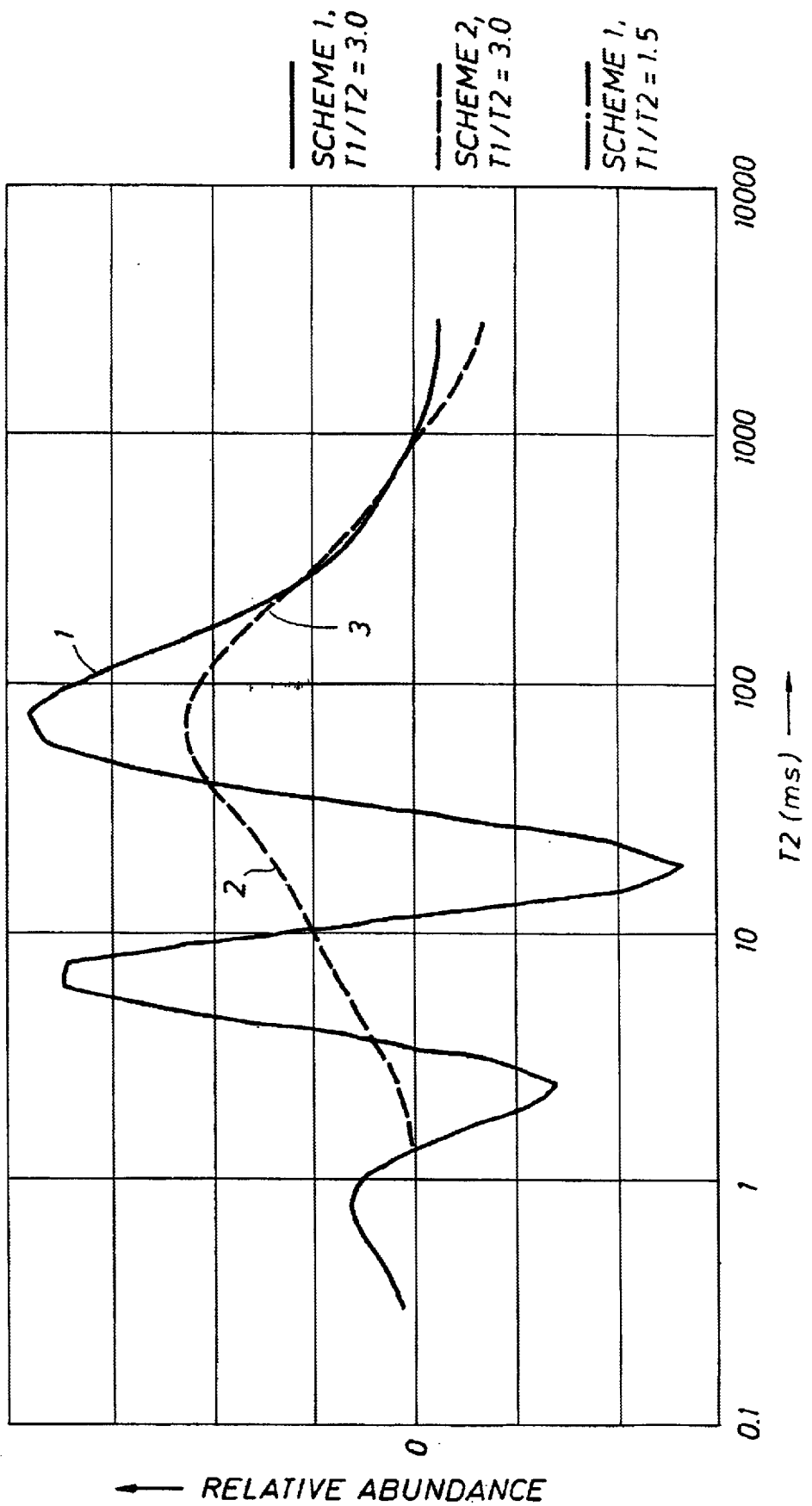
FIG. 13 is a chart illustrating $T_2$ distributions for linear inversions using the two inversion schemes of noise-free data corresponding to the $T_2$ distribution shown in FIG. 11.

Results shown in FIG. 12 are from inversions with positivity constraint. Positivity constraint is known to have regularization effects on $T_2$ inversions. This effect is stronger for the prior art inversion scheme (Scheme 1) than for the inversion scheme (Scheme 2) according to the invention. This is apparent from FIG. 13, which shows the linearly inverted (without positivity constraint) $T_2$ distributions from noise free echoes that have been simulated using the $T_2$ distributions shown in FIG. 11. FIG. 13 shows that the prior art inversion (Scheme 1; curve 1) produces large negative $T_2$ contributions and oscillations using $T_1/T_2=3.0$, whereas the new inversion scheme (Scheme 2; curve 2) using the same parameter ($T_1/T_2=3.0$) does not. Because the data used in these inversions were noise free, the negative contributions produced by the prior art inversion most likely arise from artifacts of mismatch between bursts and long-wait-time data due to incorrect polarization correction. That this artifact arises from incorrect polarization correction is corroborated by results from the prior art inversion using $T_1/T_2=1.5$ (curve 3), which does not produce the negative $T_2$ contributions. This result shows that the inversion methods according to the invention (e.g., Scheme 2) produces correct results without a positivity constraint, even when the assumed $T_1/T_2$ ratio is incorrect.

Figure 14:
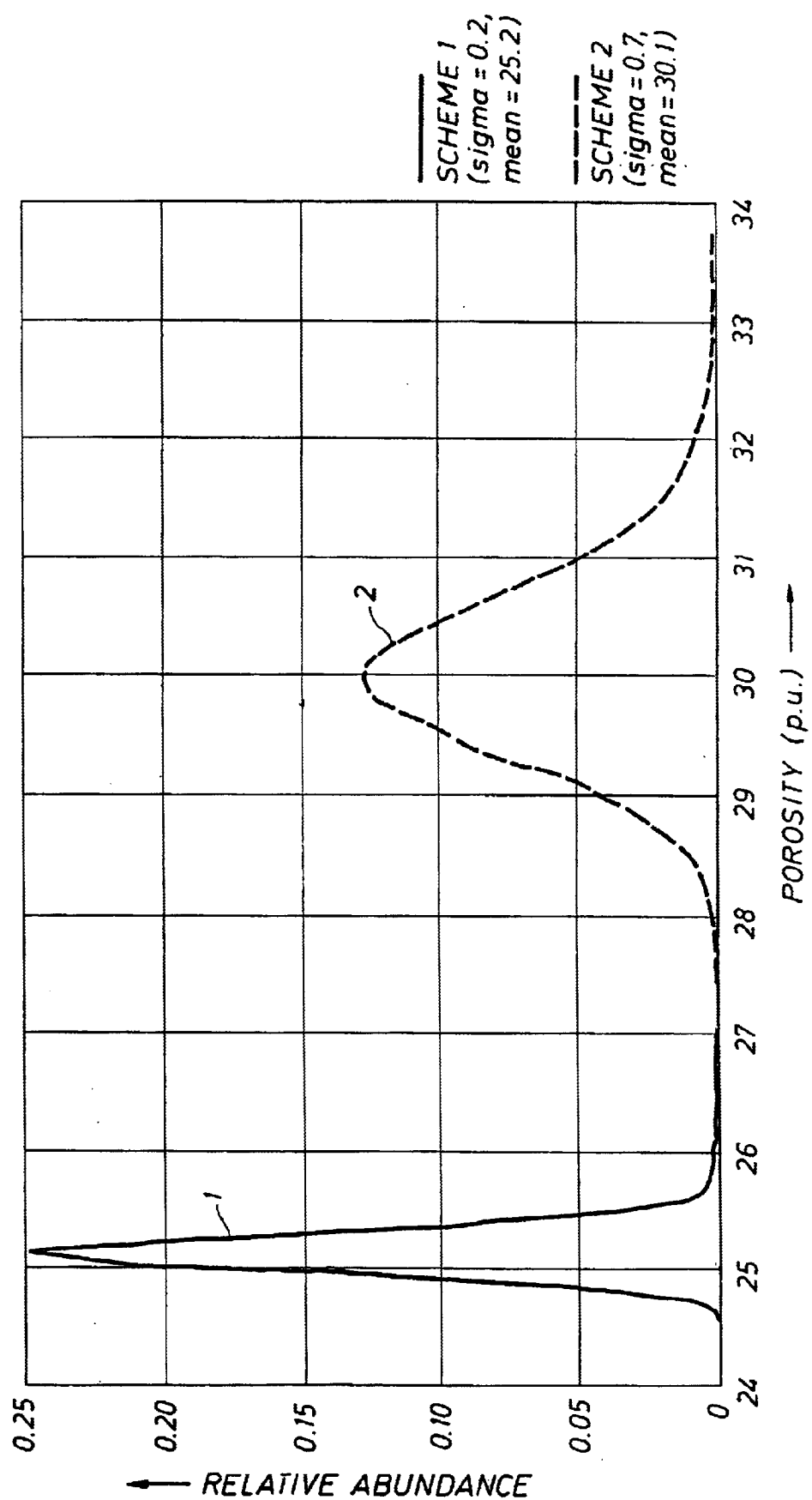
FIG. 14 is a chart illustrating the probability distributions of porosity from the two inversion schemes using the Monte Carlo simulations with the $T_2$ distribution shown in FIG. 11.

Once $T_2$ distributions are obtained from inversions, they can be used to compute formation properties, including total formation porosities. Total formation porosities may also be derived directly from the NMR measurements without first deriving the $T_2$ distributions. FIG. 14 shows the probability distributions for the total porosity computed from the standard CPMG measurement and from the burst measurements. It is apparent that the probability distribution obtained with the inversion scheme according to the invention (Scheme 2; curve 2) is wider than that obtained from the prior art inversion (Scheme 1; curve 1), indicating a larger standard deviation for the porosity using the inversion method of the invention. The computed standard deviation for the porosity throughout these two runs (computed for the 10000 samples) are 0.2 p.u. and 0.7 p.u for Scheme 1 and Scheme 2, respectively. The regularization in both cases was so chosen that the equivalent linear porosity computation (i.e., without positivity constraint) would have a standard deviation of 1 p.u.

FIG. 14 shows that the center of porosity distribution (expectation value for the porosity) from the prior art dual wait time inversion (Scheme 1; curve 1) is about 25 p.u., which is lower than that (30 p.u.) from the new dual wait time inversion according to the invention (Scheme 2; curve 2). The input data for these simulation and inversion has a porosity of 30 p.u. Therefore, the prior art inversion underestimates the porosity by about 5 p.u. The underestimation arises from the discrepancy between the $T_1/T_2$ ratio used in the inversion ($T_1/T_2$ ratio=1.5) and that used in the simulation ($T_1/T_2$ ratio=3.0). This discrepancy makes the polarization correction fail and leads to a wrong porosity determination. This is consistent with the sensitivity curves shown in FIG. 10, which clearly show that the prior art dual wait time inversion has significant sensitivities to the components with medium T2 values (about 10–100 ms).

Figure 15:
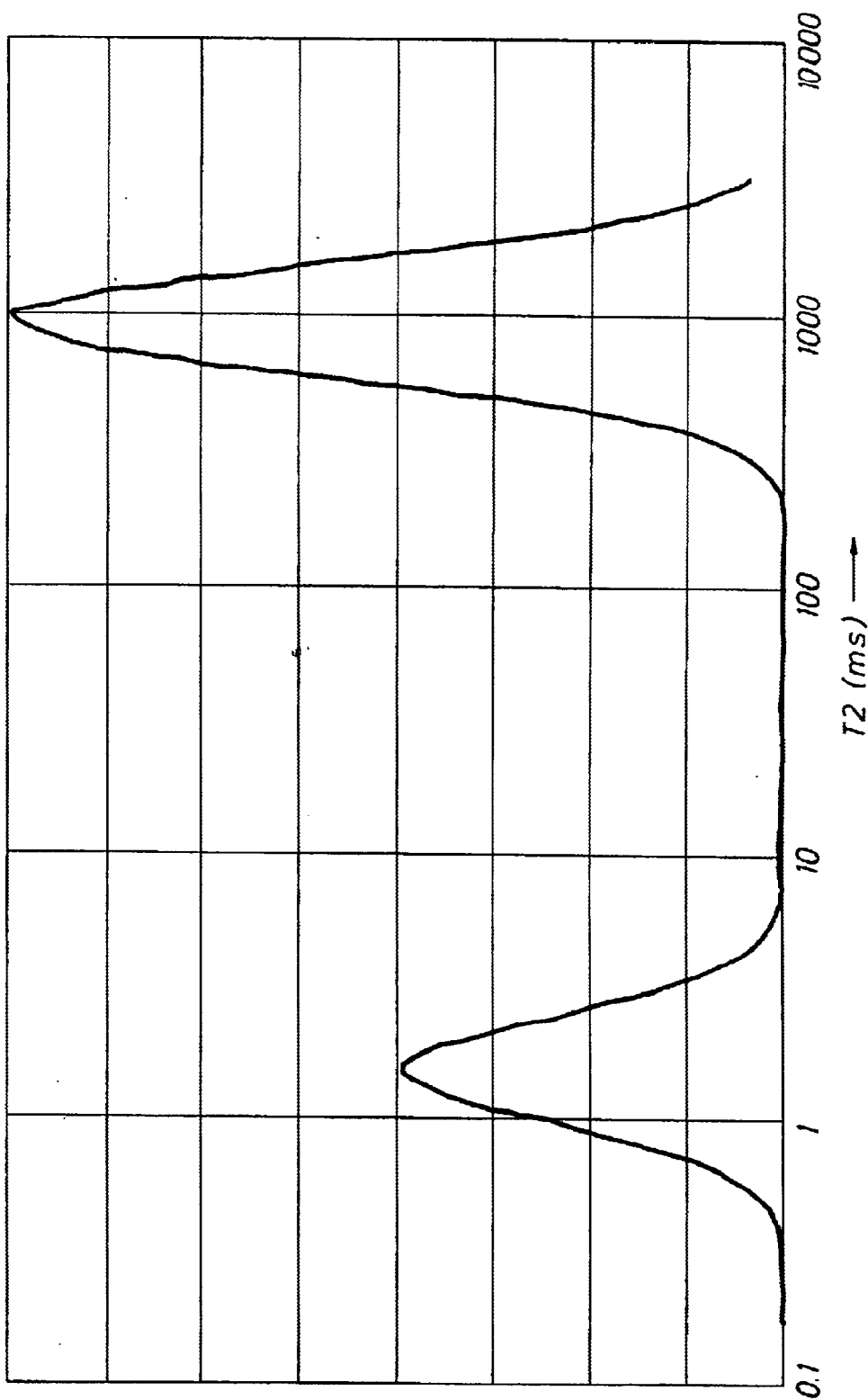
FIG. 15 is a chart illustrating the input $T_2$ distributions for the second Monte Carlo simulations.

FIG. 15 shows the input $T_2$ distribution used for another Monte Carlo simulation. The resulting averaged $T_2$ distributions for these Monte Carlo experiments are given in FIG. 16. The peak at about $T_2=2$ ms is weakened and broadened for the single wait time inversion. As expected, both dual wait time inversion schemes (Schemes 1 and 2; curves 1 and 2, respectively) reproduce this peak better than does the single wait time inversion (curve 3). The prior art dual wait time inversion (Scheme 1; curve 1) gives a narrower $T_2$ distribution than the original $T_2$ distribution (curve 4). On the other hand, the dual wait time inversion of the invention (Scheme 2; curve 2) reproduces this peak a little wider than the original data.

Figure 16:
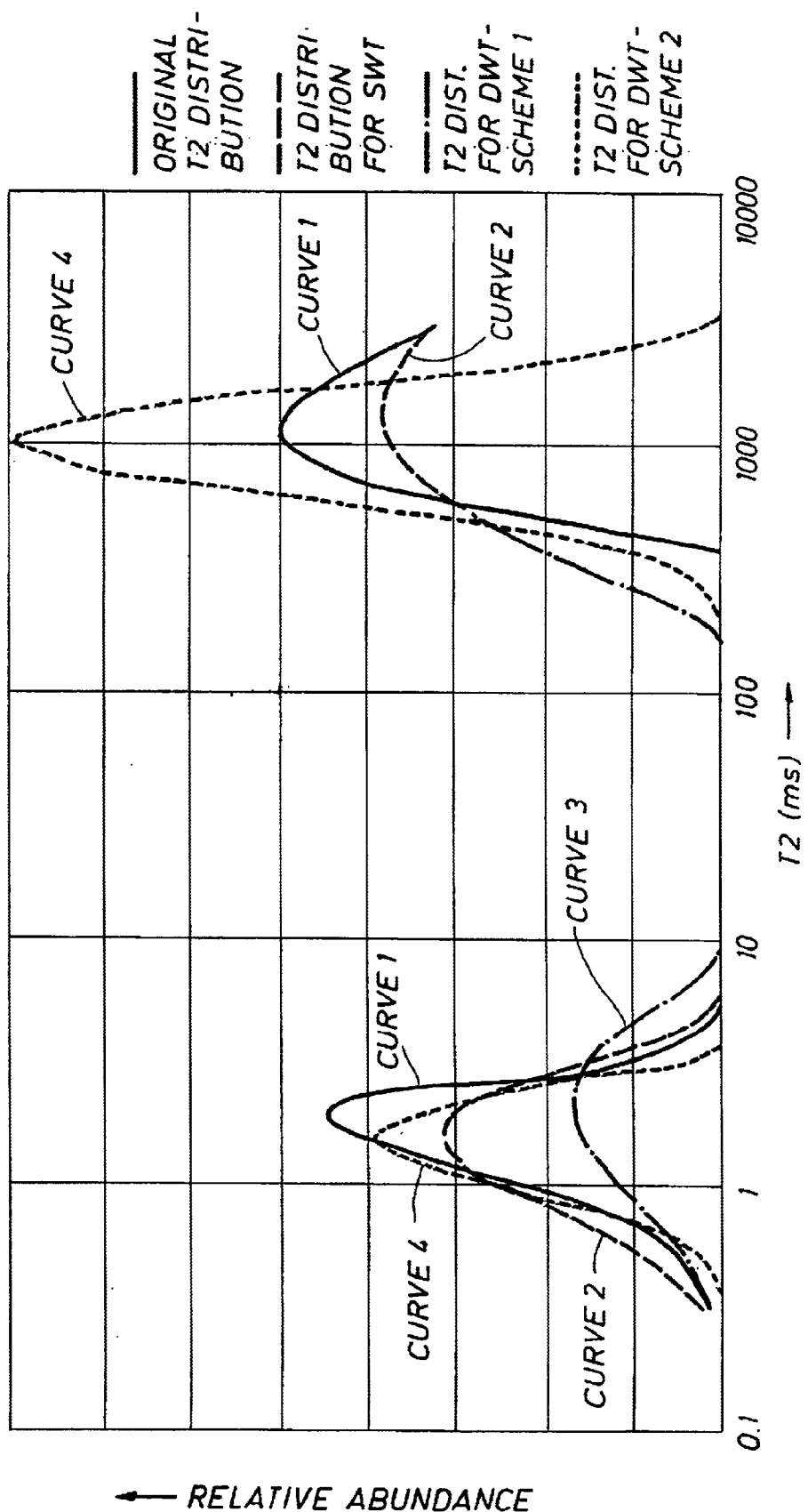
FIG. 16 shows the averaged $T_2$ distribution for the second Monte Carlo simulations for the two inversion schemes using the input $T_2$ distribution shown in FIG. 15.

For the peak at about $T_2=1000$ ms, the single wait time inversion (curve 3) is expected to produce a more reliable result because the data were collected with a long wait time, which permits the long $T_2$ components to be better polarized by the static magnetic field. The results in FIG. 16 shows that the dual wait time inversion of the invention (Scheme 2; curve 2) produces a result that is identical to that from the single wait time inversion (curve 3). This is not surprising considering that the dual wait time inversion of the invention suppresses the influence that the short wait time (bursts) measurements have on the $T_2$ components that require polarization corrections (i.e., whose polarization corrections are not negligible). Thus, the inversion of long $T_2$ components with the method of the invention uses essentially the same data from the standard CPMG measurements that are also used in the single wait time inversion. However, both inversions reproduce this peak a little wider than the input distribution suggests. This is not surprising considering that the long wait time CPMG measurement only comprised of 200 echoes and, thus, only measures 200 ms worth of data. There are insufficient data in 200 ms to accurately determine the medium and long $T_2$ components. In contrast, the prior art dual wait time inversion (Scheme 1; curve 1) produce a result that is different form the single wait time inversion (curve 3).

FIG. 17 shows the probability distributions for the porosity computed out of the $T_2$ inversions shown in FIG. 16. All three inversion schemes (the single wait time inversion, curve 3; the prior art dual wait time inversion, Scheme 1, curve 1; and the dual wait time inversion scheme according to the invention, Scheme 2, curve 2) show approximately the same standard deviation in porosity. The single wait time inversion produces a lower mean (25.1±1.0 p.u.; curve 3) than the two dual wait time schemes (about 27.7±0.8 p.u. and 28.7±0.9 p.u. for Scheme 1 and Scheme 2, curve 1 and curve 2, respectively), indicating that the fast decaying components (the peak at about 2 ms in the $T_2$ distributions, see FIG. 15) cannot be fully recovered by the single wait time inversion scheme. The input data has a porosity of 30 p.u. Thus, even the dual wait time schemes fail to recover the fast decaying components completely. This result is not surprising because a significant portion of signal intensities from the short $T_2$ components (e.g., $T_2<1$ ms) would have been lost with an inter-echo delay ($t_e$) of 1 ms used in these simulations. The difference between the results from Scheme 1 (27.7±0.8 p.u.; curve 1) and Scheme 2 (28.7±0.9 p.u.; curve 2) is due to the wrongly assumed $T_1/T_2$ ratio, which has more effect on the accuracy from the prior art inversion (Scheme 1). The difference is, however, considerably smaller than that in the previous example shown in FIG. 14, because there are no $T_2$ components between 10–200 ms in this data set (FIG. 15), whereas there is a significant portion of the $T_2$ components in this range in the previous data set (see FIG. 11). Signal intensities from the medium $T_2$ components in the 10–200 ms range will have non-negligible polarization correction in the burst data. As stated above, the prior art dual wait time inversion (Scheme 1) would show a strong dependence on the $T_1/T_2$ ratio with signals from the medium $T_2$ components (see curve 1 in FIG. 10), and an improper assumption of the $T_1/T_2$ ratio would produce an appreciable error in the $T_2$ distributions, hence the porosity distributions (see FIG. 14).

The above examples clearly show that methods of $T_2$ inversion of a long wait time CPMG measurement together with short wait time burst measurements according to embodiments of the invention produce more reliable results than do the dual wait time inversion methods known in the art. The new methods allow the common inversion of the different measurements without assuming a certain relationship between $T_1$ and $T_2$. The only assumption made in this new approach is that $T_1 = f(T_2)$ (this is common for all $T_2$ inversion schemes) and that a threshold for $T_2$ can be defined so that $T_2$ components below that threshold would have negligible polarization correction, and $T_2$ components above that threshold could be suppressed so that they would have little influence on the inversion of medium and long $T_2$ components. The inversion process according to embodiments of the invention is a linear problem, the same inversion programs already in use in the art can be used in this new scheme. Furthermore, the new scheme also does not have any problem arising from the concatenation (splicing) of two separately inverted $T_2$ distribution. The inversion scheme according to the invention can be applied both to a linear inversion or porosity estimation as well as to a full inversion with positivity constraint.

While the above examples uses measurements for $T_2$ distributions, methods of the F invention is equally applicable to NMR data that are acquired for other parameter, e.g., diffusion constants. Embodiments of the invention may be applied in any case where incomplete polarization in the NMR data needs to be corrected, irrespective of the purposes of the NMR measurements. In addition, embodiments of the invention are applicable to NMR data acquired from earth formations or from core samples removed from the earth formations. The earth formations from where the NMR data are acquired and the core samples will be generally referred to as "earth formation samples."

While the invention has been described with respect to a limited number of embodiments, those skilled in the art, having benefit of this disclosure, will appreciate that other embodiments can be devised without departing from the scope of the invention as disclosed herein. Accordingly, the scope of the invention should be limited only by the attached claims.

What is claimed is:

1. A method for determining an earth formation property from nuclear magnetic resonance measurements, comprising:
    (a) applying suppression functions to spin echoes in at least one burst measurement set to produce a modified burst data set, the suppression functions to suppress contribution of spin echoes having non-negligible polarization correction;
    (b) inverting the modified burst data set and at least one standard spin echo measurement set to produce a nuclear magnetic resonance parameter distribution, the at least one standard spin echo measurement set and the at least one burst measurement set being acquired on an earth formation sample; and
    (c) computing the earth formation property from the nuclear magnetic resonance parameter distribution.

2. The method of claim 1, wherein the inverting comprises applying the suppression functions to a forward model for the at least one burst measurement set.

3. The method of claim 1, wherein the suppression functions comprise linear combination functions.

4. The method of claim 3, wherein the linear combination functions comprise a null space of a matrix describing exponential decays of nuclear magnetizations according to acquisition parameters.

5. The method of claim 4, wherein the null space is derived from singular value decomposition.

6. The method of claim 1, wherein the at least one burst measurement set and the at least one standard spin echo measurement set are acquired with Carr-Purcell-Meiboom-Gill sequences.

7. The method of claim 1, wherein the nuclear magnetic resonance parameter comprises at least one selected from longitudinal relaxation time, transverse relaxation time, a ratio of longitudinal relaxation time to transverse relaxation time, and diffusion constant.

8. The method of claim 1, wherein the inverting is performed with a common inversion.

9. The method of claim 1, wherein the inverting is performed with regularization.

10. The method of claim 1, wherein the inverting is performed with positivity constraint.

11. The method of claim 1, wherein the earth formation property comprises one selected from total formation porosity, bound fluid volume, and free fluid volume.

12. The method of claim 1, wherein the at least one standard spin echo measurement set and the at least one burst measurement set have an identical inter-echo delay.

13. A method for determining an earth formation property from nuclear magnetic resonance measurements, comprising:
    (a) acquiring at least one standard spin echo measurement set and at least one burst measurement set on an earth formation sample;
    (b) applying suppression functions to spin echoes in at least one burst measurement set to produce a modified burst data set, the suppression functions to suppress contribution of spin echoes having non-negligible polarization correction; and
    (c) computing the earth formation property from the at least one standard spin echo measurement set and the modified burst data set.

14. The method of claim 13, wherein the suppression functions comprise linear combination functions.

15. The method of claim 14, wherein the linear combination functions comprise a null space of a matrix describing exponential decays of nuclear magnetizations according to acquisition parameters.

16. The method of claim 15, wherein the null space is derived from singular value decomposition.

17. The method of claim 13, wherein the at least one burst measurement set and the at least one standard spin echo measurement set are acquired with Carr-Purcell-Meiboom-Gill sequences.

18. The method of claim 13, wherein the at least one standard spin echo measurement set and the at least one burst measurement set have an identical inter-echo delay.

19. The method of claim 13, wherein the computing comprises inverting the at least one standard spin echo measurement set and the modified burst data set to produce a nuclear magnetic resonance parameter distribution and calculating the earth formation property from the nuclear magnetic resonance parameter distribution.

20. The method of claim 19, wherein the inverting comprises applying the suppression functions to a forward model for the at least one burst measurement set.

21. The method of claim 19, wherein the nuclear magnetic resonance parameter comprises at least one selected from longitudinal relaxation time, transverse relaxation time, a ratio of longitudinal relaxation time to transverse relaxation time, and diffusion constant.

22. The method of claim 19, wherein the inverting is performed with a common inversion.

23. The method of claim 19, wherein the inverting is performed with regularization.

24. The method of claim 19, wherein the inverting is performed with positivity constraint.

25. The method of claim 19, wherein the earth formation property comprises one selected from total formation porosity, bound fluid volume, and free fluid volume.

26. A method for determining a property of earth formations surrounding a wellbore, comprising:
 (a) inducing a static magnetic field in an area of investigation in the earth formations;
 (b) acquiring at least one standard spin echo measurement set and at least one burst measurement set by applying spin echo pulse sequences comprising radio frequency magnetic field pulses in the area of investigation and receiving spin echo signal magnitudes;
 (c) applying suppression functions to spin echoes in at least one burst measurement set to produce a modified burst data set, the suppression functions to suppress contribution of spin echoes having non-negligible polarization correction; and
 (d) computing the property of the earth formations from the at least one standard spin echo measurement set and the modified burst data set.

27. The method of claim 26, wherein the suppression functions comprise linear combination functions.

28. The method of claim 27, wherein the linear combination functions comprise a null space of a matrix describing exponential decays of nuclear magnetizations according to acquisition parameters.

29. The method of claim 28, wherein the null space is derived from singular value decomposition.

30. The method of claim 26, further comprising moving a nuclear magnetic resonance tool through the wellbore in an axial direction along the wellbore and repeating (a) and (b).

31. The method of claim 26, wherein the spin echo pulse sequences comprise Carr-Purcell-Meiboom-Gill sequences.

32. The method of claim 26, wherein the computing comprises inverting the at least one standard spin echo measurement set and the modified burst data set to produce a nuclear magnetic resonance parameter distribution and calculating the earth formation property from the nuclear magnetic resonance parameter distribution.

33. The method of claim 32, wherein the inverting comprises applying the suppression functions to a forward model for the at least one burst measurement set.

34. The method of claim 32, wherein the nuclear magnetic resonance parameter comprises at least one selected from longitudinal relaxation time, transverse relaxation time, a ratio of longitudinal relaxation time to transverse relaxation time, and diffusion constant.

35. The method of claim 32, wherein the inverting is performed with a common inversion.

36. The method of claim 32, wherein the inverting is performed with regularization.

37. The method of claim 32, wherein the inverting is performed with positivity constraint.

38. The method of claim 26, wherein the at least one standard spin echo measurement set and the at least one burst measurement set have an identical inter-echo delay.

* * * * *